United States Patent [19]

Svendsen

[11] Patent Number: 4,480,030
[45] Date of Patent: Oct. 30, 1984

[54] TRIPEPTIDE DERIVATIVES AND THEIR APPLICATION IN ASSAYING ENZYMES

[75] Inventor: Lars G. Svendsen, Reinach, Switzerland

[73] Assignee: Pentapharm A.G., Basel, Switzerland

[21] Appl. No.: 418,257

[22] Filed: Sep. 15, 1982

Related U.S. Application Data

[62] Division of Ser. No. 302,420, Sep. 16, 1981, Pat. No. 4,440,678.

[30] Foreign Application Priority Data

Feb. 12, 1980 [CH] Switzerland ............. 1130/80

[51] Int. Cl.$^3$ .............. C12Q 1/36; C12Q 1/38; C12Q 1/56; C12Q 1/00
[52] U.S. Cl. ........................... 435/13; 435/4; 435/23; 435/24; 435/29; 435/212; 435/214; 435/217; 435/810; 424/101; 424/177; 424/180; 424/183; 436/16; 436/18; 436/69; 436/86; 436/89
[58] Field of Search ............. 435/4, 13, 23, 24, 29, 435/212, 214, 217, 810; 424/101, 177, 180, 183; 436/16, 18, 69, 86, 89

[56] References Cited

U.S. PATENT DOCUMENTS

| | | | |
|---|---|---|---|
| 4,061,625 | 12/1977 | Af Ekenstam et al. | 435/13 |
| 4,070,245 | 1/1978 | Svendsen | 435/13 |
| 4,137,225 | 1/1979 | Af Ekenstam et al. | 260/112.5 R |
| 4,139,415 | 2/1979 | Yin et al. | 435/19 |
| 4,190,574 | 2/1980 | Svendsen | 435/13 |
| 4,207,232 | 6/1980 | Claeson et al. | 435/23 |
| 4,214,049 | 6/1980 | Af Ekenstam et al. | 435/23 |
| 4,229,540 | 10/1980 | Coan | 435/13 |
| 4,275,153 | 6/1981 | Gargiulo et al. | 435/13 |
| 4,276,375 | 6/1981 | Claeson et al. | 435/13 |
| 4,278,762 | 6/1981 | Svendsen | 435/13 |
| 4,279,810 | 7/1981 | Claeson et al. | 260/112.5 R |
| 4,335,204 | 6/1982 | Claeson et al. | 435/23 |

FOREIGN PATENT DOCUMENTS 4256 9/1979 European Pat. Off. .

OTHER PUBLICATIONS

*Chemical Abstracts*, vol. 94, p. 269, Abstract No. 13653f: Tran, T. H. et al., "Reactivity of a Heredity Abnormal Antithrombin III Fraction in the Inhibition of Thrombin and Factor Xa".
*Chemical Abstracts*, vol. 92, p. 397, Abstract No. 178178b: Brown, J. E. et al., "The Inhibition of the Intrinsic Generation of Activated Factor X by Heparin and Hirudin".
*Chemical Abstracts*, vol. 98, p. 317, Abstract No. 158418a: Lijnen, H. R. et al., "Heparin Binding Properties of Human Histidine-Rich Glycoprotein, Mechanism and Role in the Neutralization of Heparin in Plasma".
*Chemical Abstracts*, vol. 98, p. 317, Abstract No. 158421w: Lijnen, H. R. et al., "Neutralization of Heparin Activity by Binding to Human-Histidine-Rich Glycoprotein".
*Chemical Abstracts*, vol. 98, p. 354, Abstract No. 86892a:
Matsuo, T. et al., "Effect of Protamine on Antithrombin Activity of Heparinized Plasma".
Chen, A. L. et al., "One-Stage Assay of Heparin", *J. Lab. Clin. Med.*, May 1975, pp. 843–854.
Gomperts, E. D. et al., "The Monitoring of Heparin Activity During Extracorporeal Circulation", *S. Afr. Med. J.*, vol. 51, pp. 973–976, (1977).
Czapek, E. E. et al., "The Effect of a Sulfated Polysaccharide on Antithrombin III", *J. Lab. Clin. Med.*, vol. 95(6), pp. 783–790, (1980).
Goodnight, S. H. et al., "Measurement of Antithrombin III on Normal and Pathologic States Using Chromogenic Substrate S-2238", *Amer. Soc. of Clin. Path.*, vol. 73(5), pp. 639–647, (1980).
Elodi, S. et al., "Activation of Clotting Factors in Prothrombin Complex Concentrates as Demonstrated by Clotting Assays for Factors IXa and Xa", *Thrombosis Research*, vol. 12(5), pp. 797–807, (1978).
Shuman, M. A. et al., "The Measurement of Thrombin in Clotting Blood by Radioimmunoassay", *Journ. of Clin. Invest.*, vol. 58, pp. 1249–1258, (1976).
Walker, F. J. et al., "The Molecular Mechanisms of Heparin Action: II, Separation of Functionally Different Heparins by Affinity Chromatography", *Thrombosis Research*, vol. 14, pp. 219–230, (1979).
Seegers, W. H., "Antithrombin III, Theory and Clinical Applications", *Amer. Soc. of Clin. Path.*, vol. 69(4), pp. 367–374, (1978).
Meuleman, D. G. et al., "A Novel Anti-Thrombotic Heparinoid (ORG 10172) Devoid of Bleeding Inducing Capacity: A Survey of its Pharmacological Properties in Experimental Animal Models", *Thrombosis Research*, vol. 27, pp. 353–363, (1982).
Murphy, T. L. et al., "Endogenous Anticoagulation During Extracorporeal Perfusion: Generation of a Heparinlike Inhibitor", *Amer. Path. Soc.*, (1980), pp. H742–H750.
McDonald, M. M. et al., "Biochemical and Functional Study of Antithrombin III in Newborn Infants", *Thromb. Haemostas*, vol. 47(1), pp. 56–58, (1982).

*Primary Examiner*—Thomas G. Wiseman
*Assistant Examiner*—Deborah A. Grossman
*Attorney, Agent, or Firm*—Pennie & Edmonds

[57] ABSTRACT

A process for quantitatively assaying factor Xa from a medium by reacting the medium with tripeptide derivatives having the formula

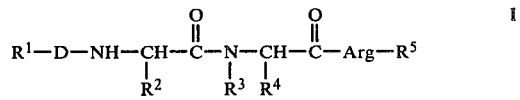

wherein $R^5$ is a chromogenic substituted amino group capable of being split off by enzymatic hydrolysis to form a colored or fluorescent product H—$R^5$. The quantity of split product H—$R^5$ released by the enzymatic action on the tripeptide derivative is determined photometrically, spectrophotometrically, fluorescence-spectrophotometrically, or electrochemically. The quantity of released split product H—$R^5$ per time unit is proportional to the quantity of enzyme present in the starting material.

9 Claims, No Drawings

TRIPEPTIDE DERIVATIVES AND THEIR APPLICATION IN ASSAYING ENZYMES

This is a division of application Ser. No. 302,420, filed Sept. 16, 1981, now U.S. Pat. No. 4,440,678.

TECHNICAL FIELD

The present invention relates to tripeptide derivatives which are very easily split by certain enzymes of the enzyme class 3.4.21., more particularly factor Xa. Therefore, the new tripeptide derivatives are intended to be used as substrates for quantitatively assaying the said enzymes, more particularly factor Xa.

BACKGROUND ART

Factor Xa is a proteolytic enzyme which is formed in the blood coagulation cascade by activation of the proenzyme factor X and which, together with phospholipid and calcium ions, proteolytically splits factor II (prothrombin) at two points of the peptide chain and converts the said factor into factor IIa (thrombin) which finally causes coagulation. In certain pathological disorders, e.g. liver diseases, vitamin deficiency, etc., and in the dicoumarol therapy, the formation of factor X is reduced. In hereditary disturbances in the synthesis of factor X the formation of factor Xa is, of course, also reduced correspondingly. Therefore, it is important to have at one's disposal a direct enzymatic assay method which allows factor Xa to be assayed photometrically in blood plasma in a simple and accurate manner.

The main methods for assaying factor Xa are the following:

(a) Biological assay method [cf. "Thrombosis and Bleeding Disorders", Nils U. Bang, Georg Thieme Verlag, p. 196 (1971)]: Factor X is activated to factor Xa by means of venom of Russel viper and calcium ions. In a onestep operation prothrombin is activated to thrombin by factor Xa in the presence of factor V and phospholipids, and thrombin converts indicator fibrinogen into fibrin. The clotting time is measured. The required factors II and V and fibrinogen are supplied by a substrate which is free from factor X. The clotting time is influenced by the degree of activation of factor X. The activation degree, under otherwise constant conditions, is a function of the concentration of factor X in the sample. This biological method allows no more than a rough assay to be carried out since the clotting time is read off subjectively by the experimentator. Furthermore, manipulated plasma is required during the preparation of which mistakes can occur. Moreover, the fibrinogen which is acting as an indicator is not formed directly, but via activated thrombin (indirect method).

(b) Biochemical mehod [cf. "Thrombosis and Bleeding Disorders", N.U. Bang, Georg Thieme Verlag, p. 196/7 (1971)]: If the factor X preparations to be tested are sufficiently pure, a more accurate assay method can be applied. Esnouf and Williams (1962) have shown that factor Xa has an esterase activity and hence splits synthetic amino acid esters. However, 50 to 100 μg of factor X are required for this assay. On the other hand, lower concentrations of factor Xa can be determined by using carbobenzoxy-phenylalaninep-nitrophenyl ester and measuring the quantity of p-nitrophenol released per time unit. This assaying method has the following disadvantages: The ester used undergoes an autohydrolysis at the applied pH of 8 and, moreover, is not specific for factor Xa since it responds also to many other enzymes. The ester is not soluble in water so that acetone is required. As a result of all these disadvantages this assaying method is inaccurate and costly.

(c) The published German patent application OS No. 25 52 570 discloses tetrapeptide derivatives which are intended to be used as substrates for assaying factor Xa. B z-Ile-Glu-Gly-Arg-pNA.HCl is disclosed as an example of a tetrapeptide derivative which is split by factor Xa with formation of p-nitroaniline. The formation of p-nitroaniline can be followed spectrophotometrically. This method of assaying factor Xa is somewhat more accurate than the above-described biological and biochemical assaying methods.

However, the tetrapeptide derivatives described in German patent application DE-OS No. 25 52 570 are not sufficiently soluble in aqueous media to allow the assay of factor Xa to be carried out at substrate saturation. In the case where extremely low concentrations of factor Xa have to be determined, e.g. in pathological plasma, the said tetrapeptide derivatives are not sufficiently sensitive to allow reasonably accurate measuring values to be obtained. If the quantity of factor Xa to be measured were increased by adding a further quantity of plasma, a precipitation of the tetrapeptide substrate would take place under the influence of plasma-proteins, and as a result it would be impossible to perform the enzyme assay.

DISCLOSURE OF INVENTION

Now, new tripeptide derivatives were found which are very easily soluble in aqueous media and which have a surprisingly high sensitivity to factor Xa.

The tripeptide derivatives of the invention have the following general formula

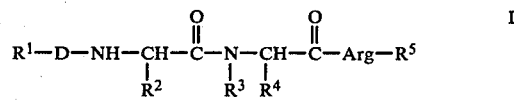

wherein $R^1$ represents an alkanoyl group which has 2 to 8 carbon atoms and which may carry an amino group in the ω-position, a phenylalkanoyl group which has 2 to 4 carbon atoms in the alkanoyl radical and the phenyl radical of which may be substituted with an amino group in the p-position, a cyclohexylcabonyl group which may be substituted with an aminomethyl radical in the 4-position, a benzoyl group which may be substituted with methyl, amino or halogen, e.g. Cl or Br, in the o- or p-position, an alkoxycarbonyl group having 1 to 8 carbon atoms in the alkoxy group, a benzyloxycarbonyl group which may be substituted with methoxy, methyl or chlorine in the p-position, an alkanesulfonyl group having 1 to 4 carbon atoms, a phenylsulfonyl group which may be methylated in the p-position or an α-naphthylsulfonyl group, $R^2$ represents a straight-chained or branched alkyl radical having 1 to 6, preferably 1 to 4, carbon atoms, a hydroxyalkyl radical having 1 to 2 carbon atoms, an alkoxyalkyl radical having 1 to 2 carbon atoms in the alkyl and 1 to 4 carbon atoms in the alkoxy, a benzyloxyalkyl radical having 1 to 2 carbon atoms in the alkyl, an ω-carboxyalkyl or ω-alkoxycarbonylalkyl radical which has 1 to 3 carbon atoms in the alkyl and the alkoxy group of which is straight-chained or branched and has 1 to 4 carbon atoms, an ω-benzyloxycarbonylalkyl radical having 1 to 3 carbon atoms in the alkyl, or a cyclohexyl-, cyclohexylemthyl-, 4-hydroxycyclohexylmethylphenyl-, benzyl-, 4-hydroxybenzyl- or imidazol-4-yl-methyl radical, $R^3$ represents a straight-chained or branched alkyl radical having 1 to 4 carbon atoms, $R^4$ represents hydrogen or a methyl or ethyl radical, and $R^5$ represents an amino group which is substituted with aromatic or heterocyclic radicals and which is capable of being split off hydrolytically with formation of a coloured or fluorescent compound H—$R^5$.

Preferably, the strongly basic guanidino group of arginine is stabilized, e.g. by protonation with a mineral acid such as HCl, HBr, $H_2SO_4$ or $H_3PO_4$, or an organic acid such as formic, acetic, propionic, lactic, citric, oxalic, tartaric, benzoic, phthalic, trichloroacetic or trifluoroacetic acid. The nature of protonation has no influence whatsoever on the sensitivity (susceptibility) of the tripeptide substrate to the enzymes.

The removable chromogenic group represented by $R^5$ in formula I can be, e.g., a p-nitrophenylamino, 1-carboxy-2-nitrophen-5-yl-amino, 1-sulfo-2-nitrophen-5-yl-amino, μ-naphthylamino, 4-methoxy-μ-naphthylamino, 5-nitro-α-naphthylamino, quinon-5-yl-amino, 8-nitro-quinon-5-yl-amino, 4-methyl-coumar-7-yl-amino or 1,3-di(methoxycarbonyl)-phen-5-yl-amino group (derived from 5-amino-isophthalic acid dimethyl ester).

The tripeptide derivatives of formula I can be prepared according to methods known per se which are described hereinafter:

(1) The chromogenic group $R^5$ is attached to the carboxy group of the C-terminal arginine, whilst its α-amino group is protected by a protective group, e.g. a carbobenzoxy or tert.-butoxycarbonyl group, and the δ-guanidyl group of arginine is protected by protonation, e.g. with HCl, nitration or tosylation. The C-terminal group $R^5$-serves also as a protective groups during the stepwise building up of the peptide chain. The remaining protective groups can be removed selectively as needed in order to attach the next amino acid derivatives until the desired peptide chain is completely built up. Finally, the remaining protective groups can be entirely removed without group $R^5$-being affected (cf. e.g. Miklos Bodansky et al., "Peptide Synthesis", Interscience Publishers, p. 163-165, 1966).

(2) First of all, the peptide chain is built up (according to Bodansky, loc. cit.) whilst the C-terminal carboxyl group of arginine is protected by a usual ester group, e.g. a methoxy, ethoxy or benzyloxy group. The ester groups can be removed by alkaline hydrolysis, except for the tert.-butoxy group which has to be removed selectively by means of trifluoroacetic acid. If the δ-guanidyl group of arginine is protonated, the said ester group is removed by trypsin, no racemization taking place in this case. Thereafter, the chromogenic group $R^5$ is introduced. If the δ-guanidino group of arginine is protected by a nitro or tosyl group and the N-terminal α-amino group of the tripeptide derivative is protected by a carbobenzoxy group or a p-methyl, p-methoxy or p-chloro-benzyloxycarbonyl group, or a tert.-butoxy group, all these protective groups are removed simultaneously. The removal can be achieved by treating the protected tripeptide derivative with anhydrous HF at room temperature, and as a result all the above-mentioned amino and δ-guanidino protective groups are removed. The removal can also be carried out by treatment with 2N HBr in glacial acetic at room temperature if the protected tripeptide derivative does not contain any nitro or tosyl as protective groups.

The tripeptide derivative of formula I are substantially more readily soluble in water than the tetrapeptide derivatives described in German patent application DE-OS No. 25 52 570 and thus allow the enzyme assays to be carried out at substrate saturation required for obtaining reliable measuring results. Besides, the tripeptide substrates of formula I are significantly more sensitive than the tetrapeptide derivatives disclosed in German patent application DE-OS No. 25 52 570 and can, therefore, also be used for assaying extremely low concentrations of factor Xa.

The published Dutch patent application OS No. 76 07 433 discloses tripeptide derivatives having the general formula H—D—$A_1$—$A_2$-$A_3$-NH—R($A_1$, $A_2$, $A_3$ =amino acid radicals) which have a high sensitivity to enzymes of enzyme class E.C. 3.4.21., e.g. thrombin and plasmin. This high sensitivity is attributed to the fact that the N-terminal D-amino acid has an unsubstituted α-amino group. Indeed, if the α-amino group of the N-terminal D-amino acid is substituted, i.e. if the hydrogen in the formula is replaced by a protective or blocking group, e.g. by benzoyl or carbobenzoxy, the sensitivity of the tripeptide derivative to enzymes of enzyme class 3.4.21. is drastically reduced. On the grounds of these findings one could have expected that the new tripeptide derivatives of formula I wherein the α-amino group of the N-terminal D-amino acid carries a protective or blocking group would not or only slightly be split by enzymes of enzme class 3.4.21. However, contrary to all expectations, the new tripeptide substrates surprisingly have a very high sensitivity to factor Xa.

A further advantage of the tripeptide substrates of the invention as compared to the tetrapeptide derivatives disclosed in German patent application DE-OS No. 25 52 570 resides in the fact that their synthesis is simpler and less costly.

The tripeptide substrates of the invention can be used for quantitively assaying certain enzymes of enzyme class E.C. 3.4.21. (c. "Enzyme Nomenclature", Elsevier Scientific Publishing Company, Amsterdam, 1973, p. 238 ff.), e.g. factor Xa in blood plasma, and via factor Xa also for the quantitative assay of other biologically important factors, e.g. factor X (proenzyme of factor Xa), antifactor Xa (=antithrombin III or heparin cofactor) or heparin in blood plasma.

These various assays can be carried out in the manner described hereinafter:

(1) Assay of factor Xa and factor X:

Citrated human plasma is used and first activated with Russel viper venom (RVV=Russel viper venom) in order to convert factor X present in the plasma into factor Xa. The following reagents are used:

Buffer: TRIS-imidazole buffer, pH 8.4, ionic strength 0.3;

RVV: Freeze-dried Russel viper venom preparation (furnished by Laboratoire Stago, 92600 Asniers s/Seine, France), dissolved in 2 ml of buffer containing $CaCl_2$ at a concentration of 0.015 M Substrate—Cbo-D-Leu-Sar-ARg-pNA.AcOH, dissolved in distilled $H_2O$, concentration: $2 \times 10^{-3}$ M.

A test cuvette is charged with 0.2 ml of RVV reagent heated to 37° C. and then with 0.02 ml of human citrated plasma. The two components are immediately mixed and then incubated for 60 seconds at 37° C. The resulting activation mixture is diluted with 1.6 ml of buffer heated to 37° C. and mixed with 0.2 ml of $2 \times 10^{-3}$ M substrate solution. Then, the change in the optical density of the mixture caused by the released p-nitroaniline is measured spectrophotometrically at a wave length of 405 nm. The measured increase in the optical density per minute is directly proportional to the quantity of factor Xa present in the activated plasma. The measured increase in the optical density per minute is also a measure for the quantity of factor X present in the starting plasma since as a result of the activation a given quantity of factor X is converted stoichiometrically into the corresponding quantity of factor Xa.

(2) Assay of antifactor Xa:

A test is prepared by diluting citrated human plasma with TRIS-imidazole buffer at a ratio of 1:10. 100 μl of a heparin solution in TRIS-imidazole buffer (containing 3 USP units of heparin per ml of buffer) are added to 100 μl of the diluted plasma, and the mixture is incubated for 2 minutes at 37° C. 100 μl of a solution of factor Xa preparation "Diagen" (furnisher: Diagnostic Reagents, Thame, Great Britain) containing 8.5 units of factor Xa per ml are added to the incubate. The mixture is incubated for 3 minutes at 37° C. The incubate is diluted with 0.6 ml of TRIS-imidazole buffer heated to 37° C. and immediately mixed with 100 μl of a $2 \times 10^{-3}$ m solution of Cbo-D-Leu-Sar-ARg-pNA.AcOH (substrate) in distilled water heated to 37° C.

In a parallel experiment a blank test sample is prepared in the same manner, but using the same volumetric quantity of buffer instead of diluted plasma.

The increase in the optical density at 405 nm is measured spectrophotometrically for both samples (test sample and blank sample). The difference between the increase in the optical density of the blank sample per minute ($\Delta OD_{blank}$/min.) and the increase in the optical density of the test sample per min. ($\Delta OD_{test}$/min.) is a measure for the quantity of factor Xa inhibited by the antifactor Xa-heparin complex and hence a measure for the quantity of antifactor Xa (=antithrombin III) present in the plasma.

(3) Assay of heparin in blood plasma:

A test sample is prepared by diluting plasma of a heparin-treated patient with TRIS-imidazole buffer at a ratio of 1:10. The diluted plasma is incubated for 1 to 2 minutes at 37° C. 100 μl of a solution of factor Xa preparation "Diagen" (furnisher: Diagnostic Reagents, Thame, Great Britain) containing 8.5 units of factor Xa per ml are added to 200 μl of the incubate, and the mixture is incubated for 3 minutes at 37° C. The incubate is diluted with 0.6 ml of TRIS-imidazole buffer heated to 37° C. and immediately mixed with 100 μl of a $2 \times 10^{-3}$ M solution of Cbo-D-Leu-Sar-Arg-pNA.AcOH (substrate) in distilled water.

In a parallel experiment a blank test sample is prepared in the same manner, but using the same quantity of corresponding diluted normal plasma (heparin-free) instead of the diluted heparinized plasma.

The increase in the optical density per minute at 405 nm is measured spectrophotometrically for both samples. The difference between the increase in the optical density of the blank sample per minute ($\Delta OD_{blank}$/min.) and the increase in the optical density of the test sample per minute $\Delta OD_{test}$/min.) is a measure for the inhibitory activity of the heparin bound to heparin-cofactor (antithrombin III).

Antifactor Xa (=heparin-cofactor or antithrombin III) alone inhibits factor Xa but slowly, so that only small quantities of factor Xa are inhibited within a short incubation period (e.g. 3 minutes). However, if antifactor Xa enters into contact with heparin, the two components form a complex which is a rapid inhibitor of factor Xa and which will completely combine with factor Xa within a short incubation time (e.g. 3 minutes).

Since the inhibition of factor Xa is proportional to the quantity of heparin present, as long as sufficient antifactor Xa is present, the quantity of heparin present in the patient's plasma can be determined by means of a calibration curve established with normal plasma and increasing quantities of added heparin on the grounds of the potentiating action of the added heparin.

In the measurement of the quantity of the coloured split product H—$R^5$ (p-nitroaniline) released in the reaction between factor Xa and the tripeptide derivatives (substrates) of the invention advantage is taken of the fact that the split product has an UV spectrum which differs from that of the substrate and is shifted towards higher wave lengths. The substrates of the invention have an absorption maximum at about 310 nm and a molar extinction coefficient of about 13,000. The absorption of the substrate at 405 nm is virtually nil. The split product H—$R^5$, i.e. p-nitroaniline, formed by enzymatic hydrolysis of the substrate has an absorption maximum at 380 nm and a molar extinction coefficient of about 13,200. At 405 nm the extinction coefficient is only moderately reduced, i.e. to about 10,400.

In the case of substrates which contain a β-naphthylamino, 4-methoxy-β-naphthylamino, coumar-7-yl-amino or isophthalylamino group as the chromogenic group, the quantity of split product H—$R^5$ released by factor Xa is measured by fluorescence-spectrophotometry. In a test system comprising factor Xa, buffer and substrate the energy-poorer emitted light is continuously measured at 400 to 470 nm after the fluorescent split product has been continuously excited by energy-richer light at 300 to 400 nm. The quantity of split product formed per time unit is a measure for the existing factor Xa activity. According to definition 1 μmole of split product formed per minute corresponds to 1 enzyme unit of factor Xa, as based on a given substrate.

The sensitivity of the above-described assaying methods can be further increased by converting the split product H—$R^5$, before measurement of its quantity, into a more intensely coloured compound by coupling with a diazo compound in the case where $R^5$ is a p-nitrophenylamino, 1-carboxy-2-nitro-phen-5-yl-amino, 1-sulfo-2-nitro-phen-5-yl-amino, 5-nitro-α-naphthylamino or 8-nitro-quinon-5-yl-amino group.

Best Mode For Carrying Out The Invention

In the following working examples the preparation of the tripeptide derivatives of the invention is described in a detailed manner. Temperatures are indicated in centigrades.

The analyses of the eluates and products obtained according to the examples were carried out by thin layer chromatography using glass plates coated with silicon dioxide gel (Merck, F 254). The thin layer chromatograms were developed by means of the following solvent system: n-butanol/acetic acid/water (3:1:1).

The following abbreviations are used:
D-Aadi = D-α-amino-adipic acid
Ac = acetyl
$Ac_2O$ = acetic anhydride
AcOH = acetic acid
Ala = L-alanine
D-Ala = D-alanine
AOA = D-α-amino-octanoic acid
Arg = L-arginine
D-Asp = D-aspartic acid
BOC = tert.-butoxycarbonyl
Bu = butyl
But = L-2-aminobutyric acid
D-But = D-2-aminobutyric acid
Bz = benzoyl
Bzl = benzyl
$Bz_2O$ = benzoic anhydride
ChA = qulnonyl amide
D-CHA = D-3-cyclohexylalanine
D-CHG = D-2-cyclohexylglycine
D-CHT = D-3-(4-hydroxycyclohexyl)-alanine = tyrosine substituted in the nucleus
Cbo = carbobenzoxy
DMF = dimethylformamide
DPA = dimethyl ester of 5-amido-isophathalic acid
TLC = thin layer chromatography or thin layer chromatogram
Et = ethyl
$Et_3N$ = triethylamine
Gly = glycine
D-Glu = D-glutamic acid
D-His = D-histidine
HMPTA = N,N,N',N',N'',N'',-hexylmethyl-phosphoric acid triamide
D-Ile = D-isoleucine
D-Leu = D-leucine
SS = solvent system
MCA = 7-amido-4-methylcoumarin
MeO = methoxy
MeOH = methanol
NA = naphthylamide
D-Nleu = D-norleucine
D-Nval = D-norvaline
OtBu = tert.-butoxy
OpNP = p-nitrophenoxy
pNA = p-nitroanilide
Pr = propyl
D-Ph'Gly = D-2-phenylglycine
D-Phe = D-phenylalanine
Sar = sarkosine = N-methylglycine
D-Ser = D-serine
TFA = trifluoroacetic acid
THF = tetrahydrofuran
D-Thr = D-threonine
Tos = p-toluenesulfonyl
D-Tyr = D-tyrosine
D-Val = D-valine If not otherwise stated, the amino acids have the L-form.

EXAMPLE 1

Cbo-D-Leu-Gly-Arg-pNA.Hbr

1a. Cbo-Arg-pNA.HCl

In a 250 ml three-necked flask 16.0 g (47 mM) of 5 Cbo-Arg-OH.HCl, which has been dried in vacuo over $P_2O_5$, were dissolved in 90 ml of abs. HMPTA at 20° in the absence of humidity. To the resulting solution there was added at room temperature first a solution of 4.74 g (47.0 mM) of $Et_3N$ in 10 ml of HMPTA and then portionwise 16.4 g (100 mM) of p-nitrophenyl isocyanate (100% excess). After a reaction time of 24 hours at 20° the major portion of HMPTA was removed by distillation in vacuo. The residue was extracted several times with 30% AcOH. The residue was discarded. The combined AcOH extracts were futher purified by passing them through a column of "Sephadex G-15" equilibrated with 30% AcOH and eluted with 30% AcOH. The fraction of the AcOH eluate which was with 30% AcOH. The fraction of the AcOH eluate which was split by treatment with trypsin with release of p-nitroaniline was freeze-dried. There was thus obtained 12.6 g of an amorphous powder which was homogeneous in the SS as shown by TLC. Elementary analysis and calculation from the empirical formula $C_{20}H_{25}N_6O_5Cl$ gave the following values: C=51.29% (51.67%), H=5.48% (5.42%), N=17.92% (18.08%), Cl=7.50% (7.63%). The values within brackets have been calculated.

1b 2HBr.H-Arg-pNA 4.65 g (10 mM) of compound 1a were treated, while stirring, with 40 ml of 2N HBr in glacial acetic acid for 45 min. at 20° in the absence of moisture. The amino acid derivative dissolved with $CO_2$ evolution. The reaction solution was added dropwise with vigorous stirring to 250 ml of absolute ether which resulted in the precipitation of 2HBr.H-Arg-pNA. The ethereal phase was sucked off, whereupon the solid phase was washed 4 times with portions of 100 ml of abs. ether in order to substantially remove benzyl bromide which had formed as a by-product as well as excess HBr and AcOH. The residue was dissolved in 50 ml of MeOH, the pH was adjusted to 4.5 by the addition of $Et_3N$, and the solution was concentrated to dryness in vacuo at 30°. The resulting product was dissolved in 75 ml of MeOH and passed through a column of "Sephadex" LH-20 (cross-linked dextran gel) equilibrated with MeOH. From a fraction of the eluate there was obtained 4.18 g (91.6% of the theory) of amorphous compound 1b which was homogeneous in the SS as shown by TLC. Elementary analysis and calculation from the empirical formula $C_{12}H_{20}N_6O_3Br_2$ gave the following values: C=31.15% (31.60%), H=4.35% (4.42%), N=18.84% (18.43%) and Br=34.81% (35.03%).

1c. Cbo-Gly-Arg-pNA.HBr 4.56 g (10 mM) of compound 1b were dissolved in 30 ml of freshly distilled DMF, and the solution was cooled to −10°; 1.40 ml (10 mM) of $Et_3N$ were added to the solution, while stirring. The formed $Et_3N$.HBr was removed by filtration and washed with a small quantity of cold DMF. 3.65 g (11 mM) of Cbo-Gly-OpNP were added at −10° to the filtrate; while stirring, and the reaction was allowed to proceed for 2-3 hours in the absence of moisture, whereby the temperature of the reaction solution gradually mounted to about 20°. The solution was again cooled to −10° and buffered with 0.70 ml (5 mM) of $Et_3N$. The reaction solution was allowed to react for about 2 hours at −10° and for three hours at room temperature. This procedure was repeated with 0.70 ml of Et$_3$N, and after 16 hours the reaction solution was concentrated to dryness in vacuo at 50°. The residue was dissolved in 75 ml of 50 % AcOH and purified by gel filtration on a column of "Sephadex" G-15 equilibrated with 50% AcOH. The fraction of the AcOH eluate which was split by treatment with trypsin with release of p-nitroaniline was concentrated to dryness in vacuo at 40°. The residue was dissolved in 150 ml of MeOH and again concentrated to dryness. The resulting residue was dried in a vacuum desiccator at 60° over P$_2$O$_5$ to obtain 5.85 g (88.3% of the theory) of amorphous compound 1 c which was homogeneous in the SS as shown by TLC. Elementary analysis and calculation from the empirical formula C$_{22}$H$_{28}$N$_7$O$_6$Br gave the following values: C =46.33% (46.65%), H =5.04% (4.98%), N =17.88% (17.31%) and Br =14.20% (14.11%).

1d. 2HBr.H—Gly—Arg—pNH 4.56 g (8 mM) of compound 1c were treated, while stirring, with 32 ml of 2N HBr in glacial acetic acid for 40 min. at 20°. The dipeptide derivative gradually dissolved with CO$_2$ evolution. The reaction solution was added dropwise with vigorous stirring to 250 ml of abs. ether, and this resulted in the precipitation of 2HBr.H—Gly—Arg—pNA. pNA. The ethereal phase was sucked off, whereupon the solid phase was washed 4 times with portions of 100 ml of abs. ether in order to substantially remove benzyl bromide which had formed as a by-product as well as excess HBr and AcOH. The residue was dissolved in 50 ml of MeOH. The pH was adjusted to 4.5 means of Et$_3$N, and the solution was concentrated to dryness in vacuo at 30°. The resulting residue was dissolved in 50 ml of MeOh and purified on a column of "Sephadex" LH-20 equilibrated with MeOH. The fraction of the MeOH eluate which was split by treatment with trypsin with release of p-nitroaniline was concentrated to dryness in vacuo at 30°. The resulting residue was dried in a vacuum desiccator at 40° over P$_2$O$_5$ to otbain 3.78 g (92.1% of the theory) of amorphous compound 1d which was homogeneous in the SS as shown by TLC. Elementary analysis and calculation from the empirical formula C$_{14}$H$_{23}$N$_7$O$_4$Br$_2$ gave the following values: C=32.31% (32.77%), H=4.59% (4.52%), N=19.47% (19.11%) and Br=30.78% (31.14%).

1e. Cbo-D-Leu-Gly-Arg-pNA.HBr 2.57 g (5 mM) of compound 1d were dissolved in 20 ml of freshly distilled DMF, and the solution was cooled to −10°; 0.70 ml (5 mM) of Et$_3$N were added to the solution, while stirring. The formed Et$_3$N.HBr was removed by filtration and washed with a small quantity of cold DMF. 2.13 g (5.5 mM) of Cbo-D-Leu-OpNP were added at −10° to the filtrate, while stirring. The reaction mixture was allowed to react for 2-3 hours in the absence of moisture, whereby the temperature of the reaction solution gradually mounted to about 20°. The solution was again cooled to −10° and buffered with 0.35 ml (2.5 mM) of Et$_3$N. The reaction solution was allowed to react for about 2 hours at −20° and for a further 3 hours at room temperature. This procedure was repeated with 0.35 ml of Et$_3$N, and after 16 hours the reaction solution was concentrated to dryness in vacuo at 50°. The residue was dissolved in 50 ml of 50% AcOH and purified by gel filtration on a column of "Sephadex" G-15 equilibrated with 50% AcOH. The fraction of the AcOH eluate which was split by treatment with trypsin with release of p-nitroaniline was concentrated to dryness in vacuo at 40°. The residue was dissolved in 100 ml of MeOH, and the solution was again concentrated to dryness. The resulting residue was dried in a vacuum desiccator at 60° over P$_2$O$_5$ to obtain 3.08 g (90.6% of the theory) of amorphous compound 1e which was homogeneous in the SS as shown by TLC. Elementary analysis and calculation from the empirical formula C$_{28}$H$_{39}$N$_8$O$_7$Br gave the following values: C=49.06% (49.49%), H=5.82% (5.78%), N=16.85% (16.49%) and Br=11.59% (11.76%).

The amino acid analysis confirmed the presence of the expected amino acids in the correct proportions: Gly : 1.00 —D-Leu : 0.99 —Arg : 0.97.

EXAMPLE 2

2b. 2HBr.H-Arg-MCA 13.0 g (25.9 mM) of commercial Cbo-Arg-MCA.HCl were deblocked according to Example 1b by means of 104 ml (208 30 mM) of a solution of 2N HBr in glacial acetic acid. The dry residue was dissolved in 400 ml of MeOH and purified on a column of "Sephadex" LH-20. The fraction of the MeOH eluate which was split by treatment with trypsin with release of 4-methyl-7-amino-coumarin was concentrated to dryness in vacuo at 30°. The resulting residue was dried in a vacuum desiccator at 40° over P$_2$O$_5$ to obtain 11.2 g (87.7% of the theory) of amorphous compound 2b which was homogeneous in the SS as shown by TLC. Elementary analysis and calculation from the empirical formula C$_{16}$H$_{23}$N$_5$O$_3$BR$_2$ gave the following values: C=39.40% (38.96%), H=4.61% (4.70%), N=14.48% (14.20%) and Br =31.90% (32.40%).

2c. Cbo-Gly-Arg-MCA.HBr 4.93g (10 mM) of compound 2b and 3.65 g (11 mM) of Cbo-Gly-OpNP were added to 75 ml of freshly distilled DMF. After cooling to −10°, there were added, while stirring, first 1.40 ml (10 mM) and then 0.70 ml (5 mM) of Et$_3$N. The mixture was allowed to react, in the absence of humidity, first for 3 hours at −10° and then for 4 hours at room temperature. The reaction solution was again cooled to −10°, buffered with 0.70 ml of Et$_3$N and stirred overnight at 20°. The reaction mixture was concentrated to dryness in vacuo at 50° and the residue was dissolved in 200 ml of 50% AcOH and purified on a column of "Sephadex" G-15. The fraction of the AcOH eluate which was split by treatment with trypsin with release of 4-methyl-7-amino-coumarin was concentrated to dryness in vacuo at 40°. The thus obtained residue was dried in a vacuum desiccator at 60° over P$_2$O$_5$ to yield 4.98 g (82.5% of the theory) of amorphous compound 2c which was homogeneous in the SS as shown by TLC. Elementary analysis and calculation from the empirical formula C$_{26}$H$_{31}$N$_6$O$_6$Br gave the following values: C=51.48% (51.75%), H=5.24%(5.18%), N=13.70% (13.93%) and Br=13.14% (13.24%).

2d. 2HBr.H-Gly-Arg-MCA 4.83 g (8 mM) of compound 2c were deblocked according to Example 1d by means of 32 ml of 2N HBr in glacial acetic acid. The resulting crude product was dissolved in 100 ml of MeOH and purified on a column of "Sephadex" LH-20. The fraction of the MeOH eluate which was split by treatment with trypsin with release of 4-methyl-7-amino-coumarin was concentrated to dryness in vacuo at 30°. The resulting residue was dried in a vacuum desiccator at 40° over P$_2$O$_5$ to give 4.05 g (92.0% of the theory) of amorphous compound 2d which was homogeneous in the SS according to TLC. Elementary analysis and calculation from the empirical formula $C_{18}H_{26}N_6O_4Br_2$ gave the following values: C=39.02% (39.29%), H=4.78% (4.76%), N=15.39% (15.27%) and Br=28.72% (29.04%)

2e. Cbo-D-Leu-Gly-Arg-MCA.HBr 2.75 g (5 mM) of compound 2d were reacted with 2.13 g (5.5 mM) of Cbo-D-Leu-OpNP in accordance with Example 1e. The resulting crude product was dissolved in 75 ml of 50% AcOH and purified on a column of "Sephadex" G-15. The fraction of the AcOH eluate which was split by treatment with trypsin with release of 4-methyl-7-amino-coumarin was concentrated to dryness in vacuo at 40°. The residue was dried in a vacuum desiccator at 60° over $P_2O_5$ to obtain 2.91 g (81.2% of the theory) of amorphous compound 2e which was homogeneous in the SS as shown by TLC. ELementary analysis and calculation from the empirical formula $C_{32}H_{42}N_7O_7Br$ gave the following values: C=53.13% (53.63%), H=6.01% (5.91%), N=13.91% (13.68%) and Br=10.88% (11.15%).

The amino acid analysis confirmed the presence of the expected amino acids in the correct proportions: Gly :1.00 —Leu : 1.02 —Arg : 0.98.

EXAMPLE 3

Cbo-D-Leu-GLY-Argo-DPA.HBr

3a. Cbo-Arg-DPA.Hcl 34.48 g (0.1 mole) of dried Cbo-Arg-OH.HCl were dissolved in a 1000 ml three-necked flask in a mixture of 150 ml of freshly distilled anhydrous DMF and 300 ml of abs. THF at 20°. To the solution, cooled to −10°, there were added, while stirring, 10.2 g (0.1 mole) of $Et_3N$ in the absence of humidity. Then a solution of 13.65 g (0.1 mole) of isobutyl chloroformate in 50 ml of THF was added dropwise to the mixture within 20 min., whereby the reaction temperature was never allowed to exceed −5°. After an additional reaction time of 10 minutes at a temperature of −10° to 5° a solution of 20.92 g (0.1 mole) of dimethyl 5-amino-isophthalate in 75 ml of DMF was added dropwise to the reaction mixture within 30 min., whereby the reaction temperature was always kept below −5°. The reaction mixture was allowed to react for another hour at 5°. Then it was stirred overnight at 20° and subsequently cooled to −15° in order to let the $Et_3N.HCl$ crystallize. The formed $Et_3N.HCl$ was filtered off and washed with a small amount of cold DMF. The filtrate and the washing solution were concentrated to dryness in vacuo at 50°. The residue was dissolved in 1000 ml of 50% AcOH and purified by gel filtration on a column of "Sephadex" G-15 equilibrated with 50% AcOH. The fraction of the AcOH eluate which was split by treatment with trypsin with release of dimethyl 5-amino-isophthalate was concentrated to dryness in vacuo at 40°. The residue was dried n a vacuum desiccator at 50° over $P_2O_5$ to obtain 24.6 g (45.9% of the theory) of amorphous compound 3a which was homogeneous in the SS as shown by TLC. Elementary analysis and calculation from the empirical formula $C_{24}H_{30}N_5O_7Cl$ gave the following values: C=53.21% (53.78%), H=5.71% (5.64%), N=13.20% (13.07%) and Cl=6.52% (6.62%).

3b. 2HBr.H-Arg-DPA 21.44 g (40 mM) of compound 3a were deblocked according to Example 1b. After the usual treatment the resulting crude product was dissolved in 250 ml of MeOH andpurified by gel filtration on a column of "Sephadex" LH-20. The fraction of the MeOH eluate which was split by treatment with trypsin with release of dimethyl 5-amino-isophthalate was concentrated to dryness in vacuo. The residue was dried in a vacuum desiccator at 40° over $P_2O_5$ to obtain 19.63 g (93.1% of the theory) of amorphous compound 3b which was homogeneous in the SS as shown by TLC. Elementary analysis and calculation from the empirical formula $C_{16}H_{25}N_5O_5Br_2$ gave the following values: C= 36.82% (36.45%), H=4.67% (4.78%), N=13.45% (13.28%) and Br=29.85% (30.31%).

3c. Cbo-Gly-Arg-DPA.HBr 5.27 g (10 mM) of compound 3b were reacted according to Example 1c with 3.65 g (11 mM) of Cbo-Gly-OpNP. The crude product obtained after the usual treatment was dissolved in 200 ml of 50% AcOH and purified on a column of "Sephadex" G-15. The fraction of the AcOH eluate which was split by treatment wit trypsin with release of dimethyl5-amino-isophthalate was concentrated to dryness in vacuo at 40°. The residue was dried in a vacuum desiccator at 60° over $P_2O_5$ to give 5.29 g (83.0% of the theory) of amorphous compound 3c which was homogeneous in the SS as shown by TLC. Elementary analysis and calculation from the empirical formula $C_{26}H_{33}N_6O_8Br$ gave the following values: C=48.50% (48.99%), H=5.28% (5.22%), N=12.92% (13.18%) and Br=12.33% (12.53%).

3d. 2HBr.H-Gly-Arg-DPA 5.10 g (8 mM) of compound 3c were deblocked according to Example 1d by means of 32 ml of 2N HBr in glacial acetic acid. The crude product obtained after the usual treatment was dissolved in 100 ml of MeOH and purified on a column of "Sephadex" LH-20. The fraction of the MeOH eluate which was split by treatment with trypsin with release of dimethyl 5-amino-isophthalate was concentrated to dryness in vacuo at 30°. The residue was dried in a vacuum desiccator at 40° over $P_2O_5$ to give 4.25 g (90.9% of the theory) of amorphous compound 3d which was homogeneous in the SS as shown by TLC. Elementary analysis and calculation from the empirical formula $C_{18}H_{28}N_6O_6$ gave the following values: C=36.85% (37.00%), H=4.90% (4.83%), N=14.72% (14.38%) and Br=26.95% (27.35).

3e. Cbo-D-Leu-Gly-Arg-DPA-HBr 2.92 g (5 mM) of compound 3d were reacted according to Example 1e with 2.13 g (5.5 mM) of Cbo-D-Leu-OpNP. The crude product obtained after the usual treatment was dissolved in 100 ml of 50% AcOH and purified on a column of "Sephadex" G-15. The fraction of the AcOH eluate which was split by treatment with trypsin with release of dimethyl 5-amino-isophthalate was concentrated to dryness in vacuo at 40°. The residue was dried in a vacuum desiccator at 60° over $P_2O_5$ to obtain 3.11 g (82.9% of the theory) of amorphous compound 3e which was homogeneous in the SS as shown by TLC. Elementary analysis and calculation from the empirical formula $C_{32}H_{44}N_7O_9Br$ gave the following values: C=50.88% (51.20%), H=5.99% (5.91%), N=13.26% (13.06%) and Br=10.48% ( 10.64%).

The amino acid analysis confirmed the presence of the expected amino acids in the correct proportions: Gly : 1.00—Leu : 1.00—Arg : 0.97.

EXAMPLE 4

4b. 2HBr.H-Arg-2-NA 9.40 g (20 mM) of commercial Cbo-Arg-2-NA.HCl were deblocked according to Example 1b with a solution of 80 ml of 2N HBr in glacial acetic acid. The product obtained after the usual treatment was dissolved in 150 ml of MeOH and purified on a column of "Sephadex" LH-20. The fraction of the MeOH eluate which was split by treatment with trypsin with release of 2-naphthylamine was concentrated to dryness in vacuo at 30°. The residue was dried in a vacuum desiccator at 40° over $P_2O_5$ to obtain 8.60 g (93.2% of the theory) of amorphous compound 4b which was homogeneous in the SS as shown by TLC. Elementary analysis and calculation from the empirical formula $C_{16}H_{23}N_5OBr_2$ gave the following values: C=42.08% (41.67%), H=5.12% (5.03%), N=14.68% (15.19%) and Br=33.96% (34.65%).

4c. Cbo-Sar-Arg-2-NA.HBr 4.6 g (10 mM) of compound 4b were reacted according to Example 1c with 3.80 g (11 mM) of Cbo-Sar-OpNP. The crude product obtained after the usual treatment was dissolved in 150 ml of 50% AcOH and purified on a column of "Sephadex" G-15. The fraction of the AcOH eluate which was split by treatment with trypsin with release of 2-naphthylamine was concentrated to dryness in vacuo at 40°. The residue was dried in a vacuum desiccator at 60° over $P_2O_5$ to obtain 4.95 g (84.5% of the theory) of amorphous compound 4c which was homogeneous in the SS as shown by TLC. Elementary analysis and calculation from the empirical formula $C_{27}H_{33}N_6O_4Br$ gave the following values: C=55.72% (55.39%), H=6.73% (5.68%), N=14.68% (14.35%) and Br=13.42% (13.65%).

4d. 2HBr.H-Sar-Arg-2-NA 4.68 g (8 mM) of compound 4c were deblocked according to Example 1d by means of 28 ml of 2N HBr in glacial acetic acid. The crude product obtained after the usual treatment was dissolved in 100 ml of MeOH and purified on a column of "Sephadex" LH-20. The fraction of the MeOH eluate which was split by treatment with trypsin with release of 2naphthylamine was concentrated to dryness in vacuo at 30°. The residue was dried in a vacuum desiccator at 40° over $P_2O_5$ to give 4.80 g (95.8% of the theory) of amorphous compound 4d which was homogeneous in the SS as shown by TLC. Elementary analysis and calculation from the empirical formula $C_{19}H_{28}N_6O_2Br_2$ gave the following values: C=43.9% (42.87%), H=5.32% (5.30%), N=16.02% (15.79%) and Br=29.68% (30.02%).

4e. Cbo-D-Leu-Sar-Arg-2-NA.HBr 2.66 g (5 mM) of compound 4d were reacted according to Example 1e with 2.13 g (5.5 mM) of Cb0—D—Leu—OpNP. The crude product obtained after the usual treatment was dissolved in 100 ml of 50% AcOH and purified on a column of "Sephadex G-15". The first main fraction of the AcOHeluate which was split by treatment with trypsin with release of 2-naphthylamine was concentrated to dryness in vacuo at 40° and dried in a vacuum desiccator at 60° over $P_2O_5$. There were thus obtained 3.01 g (86.2% of the theory of amorphous compound 4e which was homogeneous in the SS as shown by TLC. Elementary analysis and calculation from the empirical formula $C_{33}H_{44}N_7O_5Br$ gae the following values: C=57.05% (56.73%), H=6.40% (6.35%), N=14.30% (14.03%) and Br=11.12% (11.44%).

The amino acid analysis confirmed the presence of the expected amino acids in the correct proportions: Sar: 1.00—Leu: 102—Arg: 0.97.

EXAMPLE 5

Cbo-D-Leu-Sar-Arg-4-MeO-2-NA.HBr 5b. 2HBr.H-Arg-4-Meo-2-NA 10.0 g (20 mM) of commercial Cbo-Arg-4-MeO-2-Na.HCl were deblocked according to Example 1b by means of 80 ml of 2N HBr in glacial acetic acid. The crude product obtained after the usual treatment was dissolved in 150 ml of MeOH and purified on a column of "Sephadex" LH-20. The main fraction of the MeOH eluate which was split by treatment with trypsin with release of 4-methoxy-2-naphthylamine was concentrated to dryness in vacuo at 30°. The residue was dried in a vacuum desiccator at 40° over $P_2O_5$ to give 8.98 g (91.4% of the theory) of amorphous compound 5b which was homogeneous in the SS as shown by TLC. Elementary analysis and calculation from the empirical formula $C_{17}H_{25}N_5O_2Br_2$ gave the following values: C=41.22% (41.57%), H=5.19% (5.13%), N=14.40% (14.26%) and Br=32.01% (32.53%).

5c. Cbo-Sar-Arg-4-MeO-2-NA.HBr 4.91 g (10 mM) of compound 5b were reacted according to Example 1c with 3.80 g (11 mM) of Cbo-Sar-OpNP. The crude product obtained after the usual treatment was dissolved in 150 ml of 50% AcOH and purified on a column of "Sephadex" G-15. The first main fraction of the AcOH eluate which was split by treatment with trypsin with release of 4-methoxy-2-naphthylamine was concentrated to dryness in vacuo at 40°. The residue was dried in a vacuum desiccator at 60° over $P_2O_5$ to obtain 4.86 g (79.0% of the theory) of amorphous compound 5c which was homogeneous in the SS as shown by TLC. Elementary analysis and calculation from the empirical formula $C_{28}H_{35}N_6O_5Br$ gave the following values: C=54.38% (54.64%), H=5.81% (5.73%), N=13.93% (13.65%) and Br=12.75% (12.98%).

5d. 2HBr.H-Sar-Arg-4-MeO-2-NA 4.31 g (7 mM) of compound 5c were deblocked according to Example 1d with 28 ml of 2N HBr in glacial acetic acid. The crude product obtained after the usual treatment was dissolved in 100 ml of MeOH and purified on a column of "Sephadex" LH-20. The main fraction of the MeOH eluate which was split by treatment with trypsin with formation of 4-methoxy-2-naphthylamine was concentrated to dryness in vacuo at 30°. The residue was dried in a vacuum desiccator at 40° over $P_2O_5$ to obtain 3.74 g (95.0% of the theory) of amorphous compound 5d which was homogeneous in the SS as shown by TLC. Elementary analysis and calculation from the empirical formula $C_{20}H_{30}N_6O_3Br_2$ gave the following values: C=43.01% (42.72%), H=5.44% (5.38%), N=15.25% (14.95%) and Br=28.03% (28.42%).

The amino acid analysis confirmed the presence of the expected amino acids in the correct proportions: Sar: 1.00—Leu: 1.01—Arg: 0.98.

5e. Cbo-D-Leu-Sar-Arg-4-MeO-2-NA.HBr 2.81 g (5 mM) of compound 5d were reacted according to Example 1e with 2.13 g (5.5 mM) of Cbo-D-Leu-OpNP. The crude product obtained after the usual treatment was dissolved in 125 ml of 50% AcOH and purified on a column of "Sephadex" G-15. The first main fraction of the AcOH eluate which was split by treatment with trypsin with release of 4-methoxy-2-naphthylamine was concentrated to dryness in vacuo at 40°. The residue was dried in a vacuum desiccator at 60° over $P_2O_5$ to give 2.98 g (81.8% of the theory) of amorphous compound 5e which was homogeneous in the SS as shown by TLC. Elementary analysis and calculation from the empirical formula $C_{34}H_{46}N_7O_6Br$ gave the following values: C=56.28% (56.04%), H=6.34% (6.36%), N=13.75% (13.46%) and Br=10.68% (10.97%).

EXAMPLE 6

Cbo-D-Leu-Gly-Arg-pNA.AcOH 6.80 g (10 mM) of Cbo-D-Leu-Gly-Arg-pNA.HBr (prepared according to Example 1) were dissolved in 75 ml of 60% aqueous MeOH. The solution was poured on a column of "Amberlite" JRA-401 in the acetate form. The column was eluted by means of 60% aqueous MeOH, the HBr being replaced by AcOH by ion exchange. The eluate was concentrated to dryness in vacuo at 40°. After drying in the vacuum desiccator at 40° over $P_2O_5$ there were obtained 6.62 g of bromide-free Cbo-D-Leu-Gly-Arg-pNA.AcOH (99.0% of the theory). Other salts with organic acids, e.g. formic acid, propionic acid, oxalic acid, tartaric acid, citric acid, lactic acid, benzoic acid, chlorobenzoic acid, salicylic acid or phthalic acid, can also be prepared from the above named tripeptide derivative according to the same method. The ion exchanger can be e.g. "Amberlite" JRA-401 in its hydrochloride form, and the desired acid salt form can be obtained by converting the said ion exchanger into the basic OH-form by treatment with caustic soda solution and then with a solution of a 1:1 mixture of the desired organic acid and its sodium salt in 60% aqueous MeOH.

EXAMPLE 7

Tos-D-Leu-Gly-Arg-pNA.HBr 6.26 g (10 mM) of 2HBr.H-D-Leu-Gly-Arg-pNA (prepared according to Example 7f, see Table 3) were dissolved in 30 ml of distilled DMF. The solution was cooled to −15°, and first 2.80 ml (20 mM) of $Et_3N$ and immediately afterwards 1.91 g (10 mM) of tosyl chloride were added, while stirring, in the absence of humidity. After a reaction time of about 2 to 3 hours at −15°, the reaction mixture was allowed to further react overnight at room temperature. The reaction mixture was again cooled to −15°. The precipitated mixture of $Et_3N$.HBr and $Et_3N$.HCl was removed by filtration and washed with a small amount of cold DMF. The filtrate and the washing solution were combined and concentrated to dryness in vacuo at 50°. The residue was dissolved in 75 ml of 50% AcOH. The solution was purified on a column of "Sephadex" G-15 equilibrated with 50% AcOH. The main fraction of the AcOH eluate which was split by treatment with trypsin with release of p-nitroaniline was concentrated to dryness in vacuo at 40°. The residue was dissolved in 100 ml of MeOH, and the solution was again concentrated to dryness. The residue was dried in a vacuum desiccator at 60° over $P_2O_5$ to obtain 6.65 g (95.0% of the theory) of amorphous compound Tos-D-Leu-Gly-Arg-pNA.HBr which was homogeneous in the SS as shown by TLC. Elementary analysis and calculation from the empirical formula $C_{27}H_{39}N_8SO_7Br$ gave the following values: C=46.85% (46.35%), H=5.66% (5.62%), N=16.28% (16.02%), S=4.43% (4.58%) and Br=11.22% (11.42%).

Instead of using tosyl chloride as the acylation agent corresponding amounts of acetyl chloride, butyryl chloride, octanoyl chloride, benzoic acid chloride, p-methylbenzoic acid chloride, 2-chlorobenzoic acid chloride, methanesulfonyl chloride, n-butanesulfonyl chloride, benzenesulfonyl chloride, α-naphthalenesulfonyl chloride, methyl chloroformate, isobutyl chloroformate, octyl chloroformate, benzoic acid anhydride, acetic acid anhydride, phenylacetic acid-OpNP, phenylpropionic acid-OpNP, cyclohexylcarboxylic acid-OpNP, N-Cbo-4-aminomethylcyclohexylcarboxylic acid-OpNP, N-Cbo-ω-amino-n-butyric acid-OpNP, N-Cbo-ω-aminooctanoic acid-OpNP or N-Cbo-4-aminomethylbenzoic acid-OpNP can also be used.

TABLE 1

| Example | Final product | Starting products (mMole) | Method yield % | Elementary analysis | found % | calc. % | Amino acid analysis |
|---|---|---|---|---|---|---|---|
| 8 | Cbo—D-Nleu—Gly—Arg—pNA.HBr $C_{28}H_{39}N_8O_7Br$ | 1d (5 Mole) Cbo—D-Nleu—OpNP (5.5 mMole) | Example 1c 82.8 | C H N Br | 48.95 5.83 16.80 11.55 | 49.49 5.78 16.49 11.76 | Gly:Nleu:Arg 1.00:0.99:0.97 |
| 9 | Cbo—D-Nval—Gly—Arg—pNA.HBr $C_{27}H_{37}N_8O_7Br$ | 1d (5 mMole) Cbo—D-Nval—OpNP (5.5 mMole) | Example 1e 84.2 | C H N Br | 48.58 5.66 16.98 11.86 | 48.73 5.60 16.84 12.01 | Gly:Nval:Arg 1.00:1.02:0.98 |
| 10 | Cbo—D-But—Gly—Arg—pNA.HBr $C_{26}H_{35}N_8O_7Br$ | 1d (5 mMole) Cbo—D-But—OpNP (5.5 mMole) | Example 1e 83.8 | C H N Br | 47.73 5.48 17.48 12.11 | 47.93 5.41 17.20 12.26 | Gly:But:Arg 1.00:0.99:0.97 |
| 11 | Cbo—D-Ala—Gly—Arg—pNA.HBr $C_{25}H_{33}N_8O_7Br$ | 1d (5 mMole) Cbo—D-Ala—OpNP (5.5 mMole) | Example 1e 80.5 | C H N Br | 46.88 5.26 17.85 12.33 | 47.10 5.22 17.58 12.53 | Gly:Ala:Arg 1.00:1.01:0.98 |
| 12 | Cbo—D-CHA—Gly—Arg—pNA.HBr $C_{30}H_{41}N_8O_7Br$ | 1d (5 mMole) Cbo—D-CHA—OpNP (5.5 mMole) | Example 1e 82.7 | C H N Br | 50.75 5.93 16.10 11.18 | 51.07 5.86 15.88 11.32 | Gly:CHA:Arg 1.00:0.98:0.99 |
| 13 | Cbo—D-CHG—Gly—Arg—pNA.HBr $C_{29}H_{39}N_8O_7Br$ | 1d (5 mMole) Cbo—D-CHG—OpNP (5.5 mMole) | Example 1e 83.5 | C H N Br | 50.18 5.69 16.38 11.29 | 50.36 5.68 16.20 11.55 | Gly:CHG:Arg 1.00:0.97:0.99 |
| 14 | Cbo—D-CHT—Gly—Arg—pNA.HBr $C_{30}H_{41}N_8O_8Br$ | 1d (5 mMole) Cbo—D-CHT—OpNP (5.5 mMole) | Example 1e 82.0 | C H N Br | 49.62 5.80 15.76 10.88 | 49.93 5.73 15.53 11.07 | Gly:CHT:Arg 1.00:0.96:1.01 |

TABLE 1-continued

| Example | Final product | Starting products (mMole) | Method yield % | Elementary analysis | found % | calc. % | Amino acid analysis |
|---|---|---|---|---|---|---|---|
| 15 | Cbo—D-Ph'Gly—Gly—Arg—pNA.HBr C29H33N8O7Br | 1d (5 mMole) Cbo—D-Ph'Gly—OpNP (5.5 mMole) | Example 1e 81.3 | C H N Br | 50.60 4.88 16.63 11.48 | 50.81 4.85 16.35 11.66 | Gly:Ph'Gly:Arg 1.00:0.98:0.98 |
| 16 | Cbo—D-Phe—Gly—Arg—pNA.HBr C30H35N8O7Br | 1d (5 mMole) Cbo—D-Phe—OpNP (5.5 mMole) | Example 1e 80.0 | C H N Br | 51.20 5.07 16.28 11.35 | 51.51 5.04 16.02 11.42 | Gly:Phe:Arg 1.00:1.01:0.98 |
| 17 | Cbo—D-Val—Gly—Arg—pNA.HBr C27H37N8O7Br | 1d (5 mMole) Cbo—D-Val—OpNP (5.5 mMole) | Example 1e 82.8 | C H N Br | 48.71 5.62 17.08 11.90 | 48.72 5.60 16.84 12.01 | Gly:Val:Arg 1.00:1.02:1.00 |
| 18 | Cbo—D-Ile—Gly—Arg—pNA.HBr C28H39N8O7Br | 1d (5 mMole) Cbo—D-Ile—OpNP (5.5 mMole) | Example 1e 81.2 | C H N Br | 49.12 5.80 16.66 11.58 | 49.49 5.78 16.49 11.76 | Gly:Ile:Arg 1.00:0.99:0.98 |
| 19 | Cbo—D-Glu($\alpha$-OtBu)—Gly—Arg—pNA.HBr C31H43N8O9Br | 1d (5 mMole) Cbo—D-Glu($\alpha$-OtBu)—OpNP (5.5 mMole) | Example 1e 78.2 | C H N Br | 49.18 5.82 15.12 10.50 | 49.54 5.77 14.91 10.63 | Gly:Glu:Arg 1.00:0.96:0.98 |
| 20 | Cbo—D-Asp($\beta$-OtBu)—Gly—Arg—pNA.HBr C30H41N8O9Br | 1d (5 mMole) Cbo—D-Asp($\beta$-OtBu)—OpNP (5.5 mMole) | Example 1e 77.6 | C H N Br | 48.70 5.66 15.02 10.65 | 48.85 5.60 15.19 10.83 | Gly:Asp:Arg 1.00:0.97:1.00 |
| 21 | Cbo—D-His—Gly—Arg—pNA.2HBr C28H36N10O7Br2 | 1d (5 mMole) Cbo—D-His—OpNP (5.5 mMole) | Example 1e 68.5 | C H N Br | 42.71 4.70 18.05 20.12 | 42.87 4.63 17.86 20.37 | Gly:His:Arg 1.00:0.94:0.99 |
| 22 | Cbo—D-Leu—Sar—Arg—pNA.HBr C29H41N8O7Br | 22d (5 mMole) Cbo—D-Leu—OpNP (5.5 mMole) | Example 1e 82.2 | C H N Br | 50.48 6.02 16.38 11.33 | 50.22 5.96 16.16 11.52 | Sar:Leu:Arg 1.00:1.01:0.97 |
| 23 | Cbo—D-Leu—Ala—Arg—pNA.HBr C29H41N8O7Br | 23d (5 mMole) Cbo—D-Leu—OpNP (5.5 mMole) | Example 1e 83.5 | C H N Br | 50.48 6.03 16.28 11.40 | 50.22 5.96 16.16 11.52 | Ala:Leu:Arg 1.00:1.01:0.98 |
| 24 | CH3SO2—D-Nleu—Gly—Arg—pNA.AcOH C23H38N8O9S | 36f (3 mMole) CH3SO2—Cl (3.3 mMole) | Examples 7 & 6 83.1 | C H N S | 45.66 6.41 18.93 5.24 | 45.84 6.36 18.59 5.32 | Gly:Nleu:Arg 1.00:1.01:0.98 |
| 25 | isoButoxy-CO—D-Nleu—Gly—Arg—pNA.AcOH C27H44N8O9 | 36f (3 mMole) isoButoxy-CO—Cl (3.3 mMole) | Examples 7 & 6 81.4 | C H N | 51.63 7.12 18.17 | 51.91 7.10 17.94 | Gly:Nleu:Arg 1.00:1.02:0.99 |
| 26 | Cbo—D-Leu—N(Et)Gly—Arg—pNA.HBr C30H43N8O7Br | 26d (5 mMole) Cbo—D-Leu—OpNP (5.5 mMole) | Example 1e 80.6 | C H N Br | 51.30 6.15 16.10 11.12 | 50.92 6.13 15.84 11.29 | Leu:N(Et)Gly:Arg 1.00:0.98:0.99 |
| 27 | Cbo—D-Leu—N(Pr)Gly—Arg—pNA.HBr C31H45N8O7Br | 27d (5 mMole) Cbo—D-Leu—OpNP (5.5 mMole) | Example 1e 77.5 | C H N Br | 51.95 6.34 15.80 10.83 | 51.95 6.29 15.53 11.07 | Leu:N(Pr)Gly:Arg 1.00:0.96:0.98 |
| 28 | Cbo—D-CHA—Sar—Arg—pNA.HBr C31H43N8O7Br | 22d (5 mMole) Cbo—D-CHA—OpNP (5.5 mMole) | Example 1e 84.2 | C H N Br | 51.48 6.08 15.76 10.95 | 51.74 6.02 15.57 11.10 | Sar:CHA:Arg 1.00:0.98:0.98 |
| 29 | Cbo—D-CHT—Sar—Arg—pNA.HBr C31H43N8O8Br | 22d (5 mMole) Cbo—D-CHT—OpNP (5.5 mMole) | Example 1e 80.9 | C H N Br | 50.33 5.96 15.48 10.70 | 50.61 5.89 15.23 10.86 | Sar:CHT:Arg 1.00:0.97:0.99 |
| 30 | Cbo—D-Nleu—Sar—Arg—pNA.HBr C29H41N8O7Br | 22d (5 mMole) Cbo—D-Nleu—OpNP (5.5 mMole) | Example 1e 80.6 | C H N Br | 50.31 6.00 16.40 11.38 | 50.22 5.96 16.16 11.52 | Sar:Nleu:Arg 1.00:1.02:0.98 |
| 31 | Cbo—D-Nval—Sar—Arg—pNA.HBr C28H39N8O7Br | 22d (5 mMole) Cbo—D-Nval—OpNP (5.5 mMole) | Example 1e 82.7 | C H N Br | 49.33 5.80 16.74 11.62 | 49.49 5.78 16.49 11.76 | Sar:Nval:Arg 1.00:1.00:0.98 |
| 32 | Benzenesulfonyl-D-Leu—Gly—Arg—pNA.HBr C26H37N8O7SBr | 7f (5 mMole) Benzenesulfochloride (5 mMole) | Example 7g 92 | C H N S Br | 45.85 5.47 16.58 4.53 11.30 | 45.55 5.44 16.34 4.68 11.65 | Gly:Leu:Arg 1.00:1.01:0.99 |
| 33 | Methanesulfonyl-D-Leu—Gly—Arg—pNA.HBr C21H35N8O7SBr | 7f (5 mMole) Methanesulfochloride (5 mMole) | Example 7g 90.5 | C H N S Br | 40.90 5.71 18.28 5.01 12.55 | 40.45 5.66 17.97 5.14 12.82 | Gly:Leu:Arg 1.00:1.02:0.99 |

TABLE 1-continued

| Example | Final product | Starting products (mMole) | Method yield % | | Elementary analysis found % | calc. % | Amino acid analysis |
|---|---|---|---|---|---|---|---|
| 34 | α-Naphthalenesulfonyl-D-Leu—Gly—Arg—pNA.HBr C$_{30}$H$_{39}$N$_8$O$_7$SBr | 7f (5 mMole) α-Naphthalene-sulfochloride (5 mMole) | Example 7g 88 | C H N S Br | 49.38 5.40 15.55 4.25 10.62 | 48.98 5.34 15.23 4.36 10.86 | Gly:Leu:Arg 1.00:1.01:0.98 |
| 35 | n-butanesulfonyl-D-Leu—Gly—Arg—pNA.HBr C$_{24}$H$_{41}$N$_8$O$_7$SBr | 7f (5 mMole) n-Butanesulfo-chloride (5 mMole) | Example 7g 88.3 | C H N S Br | 43.55 6.28 17.08 4.73 11.84 | 43.31 6.21 16.84 4.82 12.00 | Gly:Leu:Arg 1.00:0.99:0.99 |
| 36 | Ac—D-Nleu—Gly—Arg—pNA.HBr C$_{22}$H$_{35}$N$_8$O$_6$Br | 36f (5 mMole) Acetic acid anhydride (6 mMole) | Example 7g 78.5 | C H N Br | 45.18 6.08 19.38 13.35 | 44.98 6.01 19.07 13.60 | Gly:Nleu:Arg 1.00:1.01:1.00 |
| 37 | n-Butyryl-D-Nleu—Gly—Arg—pNA.HBr C$_{24}$H$_{39}$N$_8$O$_6$Br | 36f (5 mMole) n-Butyryl-chloride (5 mMole) | Example 7g 81.2 | C H N Br | 47.03 6.45 18.41 15.38 | 46.83 6.39 18.21 15.60 | Gly:Nleu:Arg 1.00:0.97:0.99 |
| 38 | n-Octanoyl-D-Nleu—Gly—Arg—pNA.HBr C$_{28}$H$_{47}$N$_8$O$_6$Br | 36f (5 mMole) n-Octanoyl-chloride (5 mMole) | Example 7g 78.1 | C H N Br | 49.88 7.11 16.79 11.65 | 50.07 7.01 16.68 11.90 | Gly:Leu:Arg 1.00:1.01:0.98 |
| 39 | 2-Phenylacetyl-D-Leu—Sar—Arg—pNA.HBr C$_{29}$H$_{41}$N$_8$O$_6$Br | 39f (5 mMole) 2-Phenylacetic acid-OpNP (5.5 mMole) | Example 7g 80.4 | C H N Br | 51.62 6.12 16.80 11.53 | 51.40 6.10 16.54 11.79 | Sar:Leu:Arg 1.00:1.02:1.00 |
| 40 | 4-Phenylbutryl-D-Leu—Sar—Arg—pNA.HBr C$_{31}$H$_{45}$N$_8$O$_6$Br | 39f (5 mmole) 4-Phenylbutyric acid-OpNP (5.5 mMole) | Example 7g 79.2 | C H N Br | 52.99 6.47 16.05 11.18 | 52.76 6.43 15.88 11.32 | Sar:Leu:Arg 1.00:0.99:0.98 |
| 41 | Cyclohexylcarbonyl-D-Leu—Sar—Arg—pNA.HBr C$_{28}$H$_{45}$N$_8$O$_6$Br | 39f (5 mMole) Cyclohexanecarb-oxylic acid-OpNP (5.5 mMole) | Example 7g 82.3 | C H N Br | 50.51 6.81 16.75 11.81 | 50.22 6.77 16.73 11.93 | Sar:Leu:Arg 1.00:1.01:1.00 |
| 42 | Cbo—4-aminomethyl-cyclohexyl-carbonyl-D-Leu—176 Sar—Arg—pNA.HBr C$_{37}$H$_{54}$N$_9$O$_8$Br | 39f (5 mMole) Cbo—4-aminome-thylhexanecarbo-xylic acid-OpNP (5 mMole) | Example 7g 84.1 | C H N Br | 53.68 5.56 15.30 9.31 | 53.36 6.54 15.14 9.59 | Sar:Leu:Arg 1.00:0.99:0.98 |
| 43 | 4-Aminomethyl-cyclohexyl-carbonyl-bonyl-D-Leu—Sar—Arg—pNA.2HBr C$_{29}$H$_{49}$N$_9$O$_6$Br$_2$ | 42 (3 mMole) 2H HBr/AcOH | Example 1d 96.2 | C H N Br | 44.51 6.39 16.38 20.18 | 44.68 6.34 16.17 20.50 | Sar:Leu:Arg 1.00:0.99:0.98 |
| 44 | Cbo—Gly—D-Nleu—Sar—Arg—pNA.HBR C$_{31}$H$_{44}$N$_9$O$_8$Br | 44f (5 mMole) Cbo—Gly—OpNP (5.5 mMole) | Example 1c 77.8 | C H N Br | 49.88 5.96 16.93 10.44 | 49.60 5.91 16.79 10.64 | Sar:Nleu:Arg 1.00:0.98:0.99 |
| 45 | H—Gly—D-Nleu—Sar—Arg—pNA.2HBr C$_{23}$H$_{39}$N$_9$O$_6$Br$_2$ | 44 (3 mMole) 2N HBr/AcOH | Example 1d 93.6 | C H N Br | 39.88 5.69 18.18 22.52 | 39.61 5.64 18.08 22.91 | Sar:Nleu:Arg 1.00:1.00:0.98 |
| 46 | Cbo—ω-Aminobutyryl-D-Nleu—Sar—Arg—pNA.HBr C$_{33}$H$_{48}$N$_9$O$_8$Br | 44f (5 mMole) Cbo—4-Amino-butyryl-OpNP (5.5 mMole) | Example 7g 77.2 | C H N Br | 50.49 6.26 16.39 10.11 | 50.90 6.21 16.19 10.26 | Sar:Nleu:Arg 1.00:0.99:0.98 |
| 47 | ω-Aminobutyryl-D-Nleu—Sar—Arg—pNA.2HBr C$_{25}$H$_{43}$N$_9$O$_6$Br$_2$ | 46 (3 mMole) 2N HBr/AcOH | Example 1d 90.8 | C H N Br | 41.65 6.03 17.39 21.75 | 41.39 5.97 17.38 22.03 | Sar:Nleu:Arg 1.00:1.01:0.98 |
| 48 | Cbo—ω-Aminooctanoyl-D-Nleu—41 Sar—Arg—pNA.HBr C$_{37}$H$_{56}$N$_9$O$_8$Br | 44f (5 mMole) Cbo—8-Aminooc-tanoyl—tanoyl-OpNP (5.5 mMole) | Example 7g 76.2 | C H N Br | 53.09 6.80 14.88 9.45 | 53.23 6.76 15.10 9.57 | Sar:Nleu:Arg 1.00:0.98:0.99 |
| 49 | ω-Aminooctanoyl-O-Nleu—Sar—Arg—pNA.2HBr C$_{29}$H$_{51}$N$_9$O$_6$Br | 48 (3 mMole) 2N HBr/AcOH | Example 1d 92.8 | C H N Br | 44.95 6.59 16.31 20.12 | 44.56 6.58 16.13 20.45 | Sar:Nleu:Arg 1.00:0.98:1.00 |
| 50 | Bz—D-Nval—Gly—Arg—pNA.HBr C$_{26}$H$_{35}$N$_8$O$_6$Br | 50f (5 mMole) Benzoic acid an-hydride (Bz$_2$O) (7.5 mMole) | Example 7g 77.5 | C H N Br | 49.25 5.59 17.90 12.33 | 49.14 5.55 17.63 12.57 | Gly:Nval:Arg 1.00:0.99:0.98 |
| 51 | 4-Methylbenzoyl-D-Nval—Gly—Arg—pNA.HBr C$_{27}$H$_{37}$N$_8$O$_6$Br | 50f (5 mMole) 4-Methylbenzoic acid anhydride (7.5 mMole) | Example 7g 76.8 | C H N Br | 50.18 5.78 17.35 12.18 | 49.93 5.74 17.25 12.30 | Gly:Nval:Arg 1.00:1.01:0.98 |
| 52 | 2-Chlorobenzoyl-D-Nval—Gly—Arg—pNA.HCl C$_{26}$H$_{34}$N$_8$O$_6$Cl$_2$ | 50f (5 mMole) 2-Chlorobenzoic acid anhydride | Example 7g 76.4 | C H N | 50.33 5.46 18.09 | 49.92 5.48 17.91 | Gly:Nval:Arg 1.00:0.99:0.99 |

TABLE 1-continued

| Example | Final product | Starting products (mMole) | Method yield % | Elementary analysis | found % | calc. % | Amino acid analysis |
|---|---|---|---|---|---|---|---|
| 53 | 2-(4-Cbo—amino)-phenylace-tyl-D-Nval—Gly—Arg—pNA.HBr C35H44N9O8Br | (7.5 mMole) 50f (5 mMole) 2-(4-Cbo—amino)-phenylacetyl-OpNP (5.5 mMole) | Example 7g 77.9 | Cl C H N Br | 11.18 52.48 5.52 15.94 9.78 | 11.34 52.63 5.55 15.78 10.00 | Gly:Nval:Arg 1.00:0.98:0.98 |
| 54 | 2-(4-Amino)-phenylacetyl-D-Nval—Gly—Arg—pNA.2HBr C35H44N9O8Br2 | 53 (3 mMole) 2N HBr/AcOH | Example 1d 91.8 | C H N Br | 43.17 5.24 17.09 21.18 | 43.50 5.27 16.91 21.44 | Gly:Nval:Arg 1.00:0.99:1.00 |
| 55 | CH3O—CO—D-Nval—Sar—Arg—pNA.HBr C22H35N8O7Br | 55f (5 mMole) Methyl chloroformate (5.5 mMole) | Example 7g 83.6 | C H N Br | 43.59 5.92 18.76 12.95 | 43.79 5.85 18.57 13.24 | Sar:Nval:Arg 1.00:0.98:0.99 |
| 56 | CH3—(CH2)7—O—CO—D-Nval—Sar—Arg—pNA.HBr C29H49N8O7Br | 55f (5 mMole) Octyl chloroformate (5.5 mMole) | Example 7g 79.8 | C H N Br | 49.51 7.08 16.22 11.19 | 49.64 7.04 15.97 11.39 | Sar:Nval:Arg 1.00:1.00:0.98 |
| 57 | BOC—D-Leu—Gly—Arg—pNA.HBr C25H41N8O7Br | 1d (5 mMole) BOC—D-Leu—OpNP (5.5 mMole) | Example 1e 84.2 | C H N Br | 46.88 6.41 17.71 12.20 | 46.51 6.40 17.36 12.38 | Gly:Leu:Arg 1.00:1.00:0.99 |
| 58 | 4-MeO—Cbo—D-Leu—Gly—Arg—pNA.HBr C29H41N8O8Br | 1d (5 mMole) 4-MeO—Cbo—D-Leu—OpNP (5.5 mMole) | Example 1e 80.5 | C H N Br | 48.81 5.90 16.00 11.05 | 49.09 5.82 15.79 11.26 | Gly:Leu:Arg 1.00:1.01:0.98 |
| 59 | CH3O—CO—D-CHA—Gly—Arg—pNA.AcOH C27H42N8O9 | 59f (5 mMole) CH3O—CO—Cl (5.5 mMole) | Examples 7 & 6 85.6 | C H N | 52.60 6.88 18.30 | 52.08 6.80 18.00 | Gly:CHA:Arg 1.00:0.97:0.99 |
| 60 | C2H5O—CO—D-CHA—Gly—Arg—pNA.AcOH C28H44N8O9 | 59f (5 mMole) C2H5O—CO—Cl (5.5 mMole) | Examples 7 & 6 84.3 | C H N | 52.48 7.03 17.75 | 52.82 6.97 17.60 | Gly:CHA:Arg 1.00:0.98:0.98 |
| 61 | CH3SO2—D-CHA—Gly—Arg—pNA.AcOH C26H42N8O9S | 59f (5 mMole) CH3SO2—Cl (5.5 mMole) | Examples 7 & 6 86.8 | C H N S | 48.22 6.66 17.58 4.80 | 48.59 6.59 17.44 4.99 | Gly:CHA:Arg 1.00:0.97:0.97 |
| 62 | Cbo—D-Leu—Gly—Arg—2-NA.HBr C32H42N7O5Br | 62d (5 mMole) Cbo—D-Leu—OpNP (5.5 mMole) | Example 1e 79.5 | C H N Br | 55.78 6.24 14.48 11.45 | 56.14 6.18 14.32 11.67 | Gly:Leu:Arg 1.00:1.01:0.99 |
| 63 | CH3O—CO—D-Leu—Gly—Arg—2-NA.AcOH C28H41N7O7 | 62f (5 mMole) CH3O—CO—Cl (5.5 mMole) | Examples 7 & 6 75.9 | C H N | 57.02 7.10 16.83 | 57.23 7.03 16.68 | Gly:Leu:Arg 1.00:1.00:0.98 |
| 64 | CH3SO2—D-Leu—Gly—Arg—2-NA.AcOH C27H41N7O7S | 62f (5 mMole) CH3SO2—Cl (5 mMole) | Examples 7 & 6 82.1 | C H N S | 53.08 6.84 16.25 5.15 | 53.36 6.80 16.13 5.28 | Gly:Leu:Arg 1.00:1.01:0.98 |
| 65 | Cbo—D-Leu—Gly—Arg—4-MeO—2-NA.HBr C33H44N7O6Br | 65d (5 mMole) Cbo—D-Leu—OpNP (5.5 mMole) | Example 1e 84.0 | C H N Br | 55.16 6.25 13.96 11.00 | 55.46 6.21 13.72 11.18 | Gly:Leu:Arg 1.00:1.01:0.99 |
| 66 | CH3O—CO—D-Leu—Gly—Arg—4-MeO—2-NA.AcOH C29H43N7O8 | 65f (5 mMole) CH3O—CO—Cl (5.5 mMole) | Examples 7 & 6 82.4 | C H N | 56.18 7.08 16.09 | 56.39 7.02 15.87 | Gly:Leu:Arg 1.00:0.99:0.99 |
| 67 | CH3SO2—D-Leu—Gly—Arg—4-MeO—2-NA.AcOH C28H43N7O8S | 65f (5 mMole) CH3SO2—Cl (5.5 mMole) | Examples 7 & 6 77.4 | C H N S | 52.58 6.85 15.58 4.92 | 52.73 6.80 15.37 5.03 | Gly:Leu:Arg 1.00:1.01:0.98 |
| 68 | CH3O—CO—D-Leu—Gly—Arg—DPA.AcOH C28H43N7O11 | 68f (5 mMole) CH3O—CO—Cl (5.5 mMole) | Examples 7 & 6 79.3 | C H N | 51.23 6.65 15.18 | 51.45 6.63 15.00 | Gly:Leu:Arg 1.00:0.99:0.99 |
| 69 | CH3SO2—D-Leu—Gly—Arg—DPA.AcOH C27H43N7O11S | 68f (5 mMole) CH3SO2—Cl (5.5 mMole) | Examples 7 & 6 81.2 | C H N S | 47.88 6.50 14.75 4.68 | 48.13 6.43 14.55 4.76 | Gly:Leu:Arg 1.00:1.00:0.98 |
| 70 | CH3O—CO—D-Leu—Gly—Arg—MCA.AcOH C28H41N7O9 | 70f (5 mMole) CH3O—CO—Cl (5.5 mMole) | Examples 7 & 6 83.2 | C H N | 54.48 6.72 16.03 | 54.27 6.67 15.82 | Gly:Leu:Arg 1.00:1.01:1.00 |
| 71 | CH3SO2—D-Leu—Gly—Arg—MCA.AcOH C27H41N7O9S | 70f (5 mMole) CH3SO2—Cl (5.5 mMole) | Examples 7 & 6 78.4 | C H N S | 50.93 6.51 15.53 4.92 | 50.69 6.46 15.33 5.01 | Gly:Leu:Arg 1.00:0.99:0.98 |
| 72 | Cbo—D-Leu—Gly—Arg—5-NO2—1-NA.HBr C32H41N8O7Br | 72d (5 mMole) Cbo—D-Leu—OpNP (5.5 mMole) | Example 1e 75.8 | C H N Br | 52.88 5.69 15.53 10.82 | 52.68 5.66 15.36 10.95 | Gly:Leu:Arg 1.00:1.01:0.99 |
| 73 | CH3SO2—D-Leu—Gly—Arg—5-NO2—1-NA.AcOH C27H40N8O9S | 72f (5 mMole) CH3SO2—Cl (5.5 mMole) | Examples 7 & 6 80.8 | C H N | 50.08 6.24 17.29 | 49.68 6.18 17.17 | Gly:Leu:Arg 1.00:1.00:0.97 |

TABLE 1-continued

| Example | Final product | Starting products (mMole) | Method yield % | Elementary analysis | found % | calc. % | Amino acid analysis |
|---|---|---|---|---|---|---|---|
| | | | | S | 4.82 | 4.91 | |
| 74 | Cbo—D-Leu—Gly—Arg—5-ChA.HBr $C_{31}H_{41}N_8O_5Br$ | 74d (5 mMole) Cbo—D-Leu—OpNP (5.5 mMole) | Example 1e 78.5 | C H N Br | 54.28 6.07 16.48 11.54 | 54.31 6.03 16.34 11.65 | Gly:Leu:Arg 1.00:0.98:0.98 |
| 75 | CH$_3$SO$_2$—D-Leu—Gly—Arg—5-ChA.AcOH $C_{26}H_{40}N_7O_4S$ | 74f (5 mMole) CH$_3$SO$_2$—Cl (5.5 mMole) | Examples 7 & 6 76.5 | C H N S | 51.68 6.67 18.52 5.18 | 51.30 6.62 18.41 5.27 | Gly:Leu:Arg 1.00:0.99:0.98 |
| 76 | Cbo—D-Leu—Gly—Arg—8-NO$_2$—5-ChA.HBr $C_{31}H_{40}N_9O_7Br$ | 76d (5 mMole) Cbo—D-Leu—OpNP (5.5 mMole) | Example 1e 79.0 | C H N Br | 51.11 5.54 17.48 10.76 | 50.96 5.52 17.25 10.94 | Gly:Leu:Arg 1.00:0.98:0.97 |
| 77 | CH$_3$SO$_2$—D-Leu—Gly—Arg—8-NO$_2$—5-ChA.AcOH $C_{26}H_{39}N_9O_9S$ | 76f (5 mMole) CH$_3$SO$_2$—Cl (5.5 mMole) | Examples 7 & 6 75.7 | C H N S | 48.03 6.07 19.44 4.83 | 47.77 6.01 19.28 4.91 | Gly:Leu:Arg 1.00:0.98:0.97 |
| 78 | BOC—D-Nval—But—Arg—pNA.HBr $C_{26}H_{43}N_8O_7Br$ | 78d (5 mMole) BOC—D-Nval—OpNP (5.5 mMole) | Example 1e 74.6 | C H N Br | 47.45 6.61 17.24 11.88 | 47.34 6.57 16.99 12.11 | Nval:But:Arg 1.00:0.98:0.98 |
| 79 | BOC—D-Nval—N(n-Bu)Gly—Arg—pNA.HBr $C_{28}H_{47}N_8O_7Br$ | 79d (5 mMole) BOC—D-Nval—OpNP (5.5 mMole) | Example 1e 66.3 | C H N Br | 49.08 6.95 16.53 11.41 | 48.91 6.89 16.30 11.62 | Nval:Arg 1.00:0.98 |
| 80 | β-Naphthyl—SO$_2$—D-Leu—Gly—Arg—pNA.HBr $C_{30}H_{39}N_8O_7SBr$ | 7f (5 mMole) β-NA—SO$_2$—Cl (5.5 mMole) | Example 7 80.2 | C H N Br S | 49.25 5.41 15.43 10.70 4.15 | 48.98 5.34 15.23 10.86 4.36 | Gly:Leu:Arg 1.00:0.98:0.97 |
| 81 | 4-NH$_2$—Bz—D-Nleu—Gly—Arg—pNA.2HBr $C_{27}H_{39}N_9O_6Br_2$ | 36f (5 mMole) (HCl)p-NH$_2$—Bz—Cl (5.5 mMole) | Examples 7 & 6 65.0 | C H N Br | 43.68 5.32 17.13 21.05 | 43.50 5.27 16.91 21.44 | Gly:Nleu:Arg 1.00:1.02:0.98 |
| 82 | 4-Me—Cbo—D-Leu—Gly—Arg—pNA.AcOH $C_{31}H_{44}N_8O_9$ | 1d (5 mMole) 4-Me—Cbo—D-Leu—OpNP (5.5 mMole) | Examples 1e & 6 75.0 | C H N | 55.68 6.64 16.85 | 55.35 6.59 16.66 | Gly:Leu:Arg 1.00:1.01:0.99 |
| 83 | 4-Cl—Cbo—D-Leu—Gly—Arg—pNA.AcOH $C_{30}H_{41}N_8O_9Cl$ | 1d (5 mMole) 4-Cl—Cbo—D-Leu—OpNP (5.5 mMole) | Examples 1e & 6 69.3 | C H N Cl | 52.18 5.99 16.25 5.03 | 51.98 5.96 16.17 5.12 | Gly:Leu:Arg 1.00:1.01:0.98 |
| 84 | BOC—D-(α)-AOA—Gly—Arg—pNA.AcOH $C_{29}H_{48}N_8O_9$ | 1d (5 mMole) BOC—D-(α)-AOA—OpNP (5.5 mMole) | Examples 1e & 6 65.4 | C H N | 53.45 7.51 17.38 | 53.36 7.41 17.17 | Gly:Arg 1.00:0.99 |
| 85 | Cbo—D-Tyr(OBzl)—Gly—Arg—pNA.HBr $C_{38}H_{43}N_8O_8Br$ | 1d (5 mMole) Cbo—D-Tyr(OBzl)—OpNP (5.5 mMole) | Example 1e 75.5 | C H N Br | 55.26 5.33 13.85 9.58 | 55.68 5.29 13.67 9.75 | Gly:Tyr:Arg 1.00:0.97:0.99 |
| 86 | CH$_3$O—CO—D-Tyr—Gly—Arg—pNA.AcOH $C_{27}H_{36}N_8O_{10}$ | 85f (5 mMole) CH$_3$O—CO—Cl (5.5 mMole) | Examples 7 & 6 58.4 | C H N | 51.09 5.77 17.90 | 51.26 5.74 17.71 | Gly:Tyr:Arg 1.00:0.98:1.01 |
| 87 | Cbo—D-Ser(OtBu)—Gly—Arg—pNA.AcOH $C_{31}H_{44}N_8O_{10}$ | 1d (5 mMole) Cbo—D-Ser(OtBu)—OpNP (5.5 mMole) | Examples 1e & 6 73.8 | C H N | 53.78 6.48 16.45 | 54.06 6.44 16.27 | Gly:Ser:Arg 1.00:0.96:0.99 |
| 88 | Cbo—D-Ser—Gly—Arg—pNA. AcOH $C_{27}H_{36}N_8O_{10}$ | 87 (5 mMole) CF$_3$COOH (10 mMole) | 1d & 6 85.3 | C H N | 51.00 5.79 18.02 | 51.26 5.74 17.71 | Gly:Ser:Arg 1.00:0.97:1.00 |
| 89 | Cbo—D-Ser(OMe)—Gly—Arg—pNA.AcOH $C_{28}H_{38}N_8O_{10}$ | 1d (5 mMole) Cbo—D-Ser(OMe)—OpNP (5.5 mMole) | Examples 1e & 6 74.6 | C H N | 51.75 6.00 17.47 | 52.01 5.92 17.33 | Gly:Arg 1.00:0.98 |
| 90 | Cbo—D-Ser(OBzl)—Gly—Arg—pNA.AcOH $C_{34}H_{42}N_8O_{10}$ | 1d (5 mMole) Cbo—D-Ser(OBzl)—OpNP (5.5 mMole) | Examples 1e & 6 80.4 | C H N | 55.95 5.91 15.68 | 56.50 5.86 15.50 | Gly:Arg 1.00:0.99 |
| 91 | Cbo—D-Thr(OtBu)—Gly—Arg—pNA.AcOH $C_{32}H_{46}N_8O_{10}$ | 1d (5 mMole) Cbo—D-Thr(OtBu)—OpNP (5.5 mMole) | Examples 1e & 6 78.4 | C H N | 54.19 6.66 16.17 | 54.69 6.60 15.95 | Gly:Thr:Arg 1.00:0.96:0.98 |
| 92 | Cbo—D-Thr—Gly—Arg—pNA. AcOH $C_{28}H_{38}N_8O_{10}$ | 91 (5 mMole) CF$_3$COOH (10 mMole) | Examples 1d & 6 82.0 | C H N | 51.88 5.95 17.45 | 52.01 5.92 17.33 | Gly:Thr:Arg 1.00:0.97:0.98 |
| 93 | Cbo—D-Thr(OMe)—Gly—Arg—pNA.AcOH | 1d (5 mMole) Cbo—D-Thr(OMe)— | Examples 1e & 6 | C H | 52.15 6.13 | 52.72 6.10 | Gly:Arg 1.00:0.98 |

TABLE 1-continued

| Example | Final product | Starting products (mMole) | Method yield % | | Elementary analysis found % | calc. % | Amino acid analysis |
|---|---|---|---|---|---|---|---|
| | $C_{29}H_{40}N_8O_{10}$ | OpNP (5.5 mMole) | 75.5 | N | 17.20 | 16.96 | |
| 94 | Cbo—D-Thr(OBzl)—Gly—Arg—pNA.AcOH $C_{35}H_{44}N_8O_{10}$ | 1d (5 mMole) Cbo—D-Thr(OBzl)—OpNP (5.5 mMole) | Examples 1e & 6 81.2 | C H N | 56.50 6.07 15.45 | 57.06 6.02 15.21 | Gly:Arg 1.00:1.00 |
| 95 | Cbo—D-Asp—Gly—Arg—pNA $C_{26}H_{32}N_8O_9$ | 20 (5 mMole) $CF_3COOH$ (15 mMole) | Examples 1d & 6 85.0 | C H N | 51.66 5.43 18.95 | 52.00 5.37 18.66 | Gly:Asp:Arg 1.00:0.98:1.01 |
| 96 | Cbo—D-Glu—Gly—Arg—pNA $C_{27}H_{34}N_8O_9$ | 19 (5 mMole) $CF_3COOH$ (15 mMole) | Examples 1d & 6 82.4 | C H N | 52.21 5.61 18.48 | 52.76 5.58 18.23 | Gly:Glu:Arg 1.00:0.97:0.99 |
| 97 | Cbo—D-Glu(γ-OMe)—Gly—Arg—pNA.AcOH $C_{30}H_{40}N_8O_{11}$ | 1d (5 mMole) Cbo—D-Glu(γ-OMe)—OpNP (5.5 mMole) | Examples 1e & 6 78.6 | C H N | 51.84 5.89 16.47 | 52.32 5.85 16.27 | Gly:Glu:Arg 1.00:1.01:0.98 |
| 98 | Cbo—D-Asp(β-OMe)—Gly—Arg—pNA.AcOH $C_{29}H_{38}N_8O_{11}$ | 1d (5 mMole) Cbo—D-Asp(β-OMe)—OpNP (5.5 mMole) | Examples 1e & 6 78.9 | C H N | 51.48 5.71 16.93 | 51.63 5.68 16.61 | Gly:Asp:Arg 1.00:1.02:1.00 |
| 99 | Cbo—D-Glu(γ-OBzl)—Gly—Arg—pNA.AcOH $C_{35}H_{42}N_8O_{11}$ | 1d (5 mMole) Cbo—D-Glu(γ-OBzl)—OpNP (5.5 mMole) | Examples 1e & 6 76.7 | C H N | 55.38 5.68 15.09 | 55.99 5.64 14.93 | Gly:Glu:Arg 1.00:0.98:0.99 |
| 100 | Cbo—D-Asp(β-OBzl)—Gly—Arg—pNA.AcOH $C_{34}H_{40}N_8O_{11}$ | 1d (5 mMole) Cbo—D-Asp(β-OBzl)—OpNP (5.5 mMole) | Examples 1e & 6 74.8 | C H N | 55.03 5.51 15.48 | 55.43 5.47 15.21 | Gly:Asp:Arg 1.00:0.99:0.97 |
| 101 | Cbo—D-Aadi(δ-OtBu)—Gly—Arg—pNA.AcOH $C_{34}H_{48}N_8O_{11}$ | 1d (5 mMole) Cbo—D-Aadi(δ-OtBu)—OpNP (5.5 mMole) | Examples 1e & 6 71.5 | C H N | 54.13 6.57 15.29 | 54.83 6.50 15.05 | Gly:Arg 1.00:0.98 |
| 102 | Cbo—D-Aadi—Gly—Arg—pNA $C_{28}H_{36}N_8O_9$ | 101 (5 mMole) $CF_3COOH$ (15 mMole) | Examples 1d & 6 81.1 | C H N | 52.97 5.83 18.05 | 53.50 5.77 17.83 | Gly:Arg 1.00:0.99 |
| 103 | Cbo—D-Aadi(δ-OBzl)—Gly—Arg—pNA.AcOH $C_{37}H_{46}N_8O_{11}$ | 1d (5 mMole) Cbo—D-Aadi(δ-OBzl)—OpNP (5.5 mMole) | Examples 1e & 6 73.9 | C H N | 56.53 6.00 14.65 | 57.06 5.95 14.39 | Gly:Arg 1.00:0.99 |

TABLE 2

| Ex. | | Starting product (mMole) | Method yield % | | Elementary analysis found % | calc. % |
|---|---|---|---|---|---|---|
| | Dipeptide intermediate | | | | | |
| 22c | Cbo—Sar—Arg—pNA.HBr $C_{23}H_{30}N_7O_6Br$ | 1b (10 mMole) Cbo—Sar—OpNP (11 mMole) | Example 1c 84.1 | C H N Br | 47.88 5.25 17.08 13.50 | 47.59 5.21 16.89 13.77 |
| 22d | 2HBr.H—Sar—Arg—pNA $C_{15}H_{25}N_7O_4Br_2$ | 22c (7 mMole) 2N HBr/AcOH | Example 1d 91.2 | C H N Br | 34.50 4.82 18.91 30.06 | 34.17 4.78 18.60 30.31 |
| 23c | Cbo—Ala—Arg—pNA.HBr $C_{23}H_{30}N_7O_6Br$ | 1b (10 mMole) Cbo—Ala—OpNP (11 mMole) | Example 1c 83.6 | C H N Br | 47.69 5.28 16.95 13.46 | 47.59 5.21 16.89 13.77 |
| 23d | 2HBr.H—Ala—Arg—pNA $C_{15}H_{25}N_7O_4Br_2$ | 23c (7 mMole) 2N HBr/AcOH | Example 1d 93.6 | C H N Br | 34.28 4.79 18.90 29.88 | 34.17 4.78 18.60 30.31 |
| 26c | Cbo—N(Et)Gly—Arg—pNA.HBr $C_{24}H_{32}N_7O_6Br$ | 1b (10 mMole) Cbo—N(Et)Gly—OpNP (11 mMole) | Example 1c 86.0 | C H N Br | 48.62 5.48 16.55 13.25 | 48.49 5.43 16.49 13.44 |
| 26d | 2HBr.H—N(Et)Gly—Arg—pNA $C_{16}H_{27}N_7O_4Br_2$ | 26c (7 mMole) 2N HBr/AcOH | Example 1d 94.0 | C H N Br | 35.70 5.09 18.30 29.22 | 35.51 5.03 18.12 29.53 |
| 27c | Cbo—N(Pr)Gly—Arg—pNA.HBr $C_{25}H_{34}N_7O_6Br$ | 1b (10 mMole) (Cbo—N(Pr)Gly—OpNP (11 mMole) | Example 1c 82.5 | C H N Br | 50.08 5.69 16.36 12.88 | 49.35 5.63 16.11 13.13 |
| 27d | 2HBr.H—N(Pr)Gly—Arg—pNA $C_{17}H_{29}N_7O_4Br_2$ | 27c (7 mMole) 2N HBr/AcOH | Example 1d 88.5 | C H N | 36.68 5.31 17.96 | 36.77 5.26 17.66 |

TABLE 2-continued

| Ex. | Starting product (mMole) | Method yield % | Elementary analysis | | |
|---|---|---|---|---|---|
| | | | | found % | calc. % |
| | | | Br | 28.58 | 28.78 |
| Amino acid or dipeptide intermediate | | | | | |
| 62c Cbo—Gly—Arg—2-Na.HBr $C_{26}H_{31}N_6O_4Br$ | 4b (5 mMole) Cbo—Gly—OpNP (5.5 mMole) | Example 4c 75.6 | C H N Br | 54.24 5.52 14.95 13.75 | 54.64 5.47 14.71 13.98 |
| 62d 2HBr.H—Gly—Arg—2-NA $C_{18}H_{26}N_6O_2Br_2$ | 62c (5 mMole) 2N HBr/AcOH | Example 4d 90.6 | C H N Br | 41.50 5.10 16.62 30.15 | 41.72 5.06 16.22 30.84 |
| 65c Cbo—Gly—Arg—4-MeO—2-NA.HBr $C_{27}H_{33}N_6O_5Br$ | 5b (5 mMole) Cbo—Gly—OpNP (5.5 mMole) | Example 5c 88.4 | C H N Br | 53.41 5.55 14.22 12.95 | 53.91 5.53 13.97 13.28 |
| 65d 2HBr.H—Gly—Arg—4-MeO—2-NA $C_{19}H_{28}N_6O_3Br_2$ | 65c (5 mMole) 2N HBr/AcOH | Example 5d 90.9 | C H N Br | 41.32 5.19 15.54 28.85 | 41.62 5.15 15.33 29.15 |
| 72a Cbo—Arg—5-NO$_2$—1-NA.HCl $C_{24}H_{27}N_6O_5Cl$ | Cbo—Arg—OH.HCl (25 mMole) 5-NO$_2$—1-naphthyl- amine (25 mMole) | Example 3a 38.7 | C H N Cl | 55.65 5.31 16.54 6.77 | 55.98 5.28 16.32 6.89 |
| 72b 2HBr.H.Arg—5-NO$_2$—1-NA $C_{16}H_{22}N_6O_3Br_2$ | 72a (5 mMole) 2N HBr/AcOH | Example 4b 88.5 | C H N Br | 37.85 4.41 16.78 31.10 | 37.96 4.38 16.60 31.57 |
| 72c Cbo—Gly—Arg—5-NO$_2$—1-NA.HBr $C_{26}H_{30}N_7O_6Br$ | 72b (3 mMole) Cbo—Gly—OpNP (3.3 mMole) | Example 4c 78.6 | C H N Br | 50.25 4.99 16.10 12.76 | 50.66 4.91 15.91 12.96 |
| 72d 2HBr.H—Gly—Arg—5-NO$_2$—1-NA $C_{18}H_{25}N_7O_4Br_2$ | 72c (2.5 mMole) 2N HBr/AcOH | Example 1d 91 | C H N Br | 38.17 4.51 17.63 28.00 | 38.38 4.47 17.41 28.37 |
| 74a Cbo—Arg—5-ChA.HCl $C_{23}H_{27}N_6O_3Cl$ | Cbo—Arg—OH.HCl (25 mMole) 5-aminoquinoline (25 mMole) | Example 3a 31.9 | C H N Cl | 58.09 5.84 18.06 7.44 | 58.66 5.78 17.85 7.53 |
| 74b 2HBr.H—Arg—5-ChA $C_{15}H_{22}N_6OBr_2$ | 74a (5 mMole) 2N HBr/AcOH | Example 1d 81.8 | C H N Br | 38.75 4.83 18.45 33.88 | 38.98 4.80 18.18 34.58 |
| 74c Cbo—Gly—Arg—5-ChA.HBr $C_{25}H_{30}N_7O_4Br$ | 74b (3 mMole) Cbo—Gly—OpNP (3.3 mMole) | Example 4c 68.5 | C H N Br | 52.17 5.32 17.17 13.63 | 52.45 5.28 17.13 13.96 |
| 74d 2HBr.H—Gly—Arg—5-ChA $C_{17}H_{25}N_7O_2Br_2$ | 74c (2.5 mMole) 2N HBr/AcOH | Example 1d 78.3 | C H N Br | 39.19 4.90 19.11 30.45 | 39.32 4.85 18.88 30.78 |
| 76a Cbo—Arg—8-NO$_2$—5-ChA.HCl $C_{23}H_{26}N_7O_5Cl$ | Cbo—Arg—OH.HCl (25 mMole) 5-NH$_2$-8-NO$_2$- quinoline (25 mMole) | Example 3a 33.0 | C H N Cl | 53.14 5.11 19.21 6.80 | 53.54 5.08 19.00 6.87 |
| 76b 2HBr.H—Arg—8-NO$_2$—5-ChA $C_{15}H_{21}N_7O_3Br_2$ | 76a (5 mMole) 2N HBr/AcOH | Example 1d 84.2 | C H N Br | 35.42 4.20 19.50 30.99 | 35.52 4.17 19.33 31.51 |
| 76c Cbo—Gyl—Arg—8-NO$_2$—5-ChA.HBr $C_{25}H_{29}N_8O_6Br$ | 76b (3 mMole) Cbo—Gly—OpNP (3.3 mMole) | Example 4c 68.5 | C H N Br | 48.32 4.77 18.28 12.74 | 48.63 4.73 18.15 12.94 |
| 76d 2HBr.H—Gly—Arg—8-NO$_2$—5-ChA $C_{17}H_{24}N_8O_4Br_2$ | 76c (2.5 mMole) 2N HBr/AcOH | Example 1d 76.9 | C H N Br | 36.00 4.33 20.05 27.95 | 36.19 4.29 19.86 28.32 |
| 78c Cbo—But—Arg—pNA.HBr $C_{24}H_{32}N_7O_6Br$ | 1b (5 mMole) Cbo—But—OpNP (5.5 mMole) | Example 1c 80.4 | C H N Br | 48.55 5.47 16.75 13.20 | 48.49 5.43 16.49 13.44 |
| 78d 2HBr.H—But—Arg—pNA $C_{16}H_{27}N_7O_4Br_2$ | 78c (3 mMole) 2N HBr/AcOH | Example 1d 84.8 | C H N Br | 35.27 5.03 18.38 29.25 | 35.51 5.03 18.12 29.53 |
| 79c Cbo—N(n-Bu)Gly—Arg—pNA.HBr $C_{26}H_{36}N_7O_6Br$ | 1b (5 mMole) Cbo—N(n-Bu)Gly— | Example 1c 68.2 | C H | 49.75 5.85 | 50.16 5.83 |

TABLE 2-continued

| Ex. | | Starting product (mMole) | Method yield % | Elementary analysis | | |
|---|---|---|---|---|---|---|
| | | | | | found % | calc. % |
| 79d | 2HBr.H—N(n-Bu)Gly—Arg—pNA $C_{18}H_{31}N_7O_4Br_2$ | OpNP (5.5 mMole) 79c (2.5 mMole) 2N HBr/AcOH | Example 1d 80.7 | N Br C H N Br | 15.90 12.63 37.88 5.54 17.50 27.70 | 15.75 12.84 37.97 5.49 17.22 28.07 |

TABLE 3

| Ex. | Tripeptide intermediates | Starting products (mMole) | Method yield % | Elementary analysis | | |
|---|---|---|---|---|---|---|
| | | | | | found % | calc. % |
| 7f | 2HBr.H—D-Leu—Gly—Arg—pNa $C_{20}H_{34}N_8O_5Br_2$ | 1 (5 mMole) 2N HBr/AcOH | Example 2d 96.3 | C H N Br | 38.09 5.41 17.95 25.42 | 38.35 5.47 17.89 25.51 |
| 36f | 2HBr.H—D-Nleu—Gly—Arg—pNA $C_{20}H_{34}N_8O_5Br_2$ | 8 (5 mMole) 2N HBr/AcOH | Example 2d 93.4 | C H N Br | 38.18 5.52 18.06 25.20 | 38.35 5.47 17.89 25.51 |
| 39f | 2HBr.H—D-Leu—Sar—Arg—pNA $C_{21}H_{36}N_8O_5Br_2$ | 22 (5 mMole) 2N HBr/AcOH | Example 2d 92.1 | C H N Br | 39.15 5.70 17.81 24.81 | 39.39 5.67 17.50 24.96 |
| 44f | 2HBr.H—D-Nleu—Sar—Arg—pNA $C_{21}H_{36}N_8O_5Br_2$ | 30 (5 mMole) 2N HBr/AcOH | Example 2d 96.2 | C H N Br | 39.08 5.63 17.75 24.70 | 39.39 5.67 17.50 24.96 |
| 50f | 2HBr.H—D-Nval—Gly—Arg—pNA $C_{19}H_{32}N_8O_5Br_2$ | 9 (5 mMole) 2N HBr/AcOH | Example 2d 91.8 | C H N Br | 37.02 5.33 18.55 25.88 | 37.27 5.27 18.30 26.10 |
| 55f | 2HBr.H—D-Nval—Sar—Arg—pNA $C_{20}H_{34}N_8O_5Br_2$ | 31 (5 mMole) 2N HBr/AcOH | Example 2d 95.5 | C H N Br | 38.38 5.54 18.10 25.25 | 38.35 5.47 17.89 25.51 |
| 59f | 2HBr.H—D-CHA—Gly—Arg—pNA $C_{23}H_{38}N_8O_5Br_2$ | 12 (5 mMole) 2N HBr/AcOH | Example 1d 82.3 | C H N Br | 41.50 5.77 17.07 23.71 | 41.45 5.75 16.82 23.98 |
| 62f | 2HBr.H—D-Leu—Gly—Arg—2-NA $C_{24}H_{36}N_7O_3Br_2$ | 62 (5 mMole) 2N HBr/AcOH | Example 1d 78.5 | C H N Br | 45.43 5.81 15.81 25.05 | 45.73 5.76 15.55 25.35 |
| 65f | 2HBr.H—D-Leu—Gly—Arg—4-MeO—2-NA $C_{25}H_{38}N_7O_4Br_2$ | 65 (5 mMole) 2N HBr/AcOH | Example 1d 76.9 | C H N Br | 45.18 5.83 15.03 23.85 | 45.47 5.80 14.85 24.20 |
| 68f | 2HBr.H—D-Leu—Gly—Arg—DPA $C_{24}H_{38}N_7O_7Br_2$ | 3e (5 mMole) 2N HBr/AcOH | Example 1d 76.9 | C H N Br | 41.20 5.55 14.23 22.66 | 41.39 5.50 14.08 22.95 |
| 70f | 2HBr.H—D-Leu—Gly—Arg—MCA $C_{24}H_{36}N_7O_5Br_2$ | 2e (5 mMole) 2N HBr/AcOH | Example 1d 80.8 | C H N Br | 43.17 5.51 15.00 23.81 | 43.52 5.48 14.80 24.13 |
| 72f | 2HBr.H—D-Leu—Gly—Arg—5-NO$_2$—1-NA $C_{24}H_{35}N_8O_5Br_2$ | 72 (5 mMole) 2N HBr/AcOH | Example 1d 68.4 | C H N Br | 42.51 5.24 16.83 23.45 | 42.68 5.22 16.59 23.66 |
| 74f | 2HBr.H—D-Leu—Gly—Arg—5-ChA $C_{23}H_{35}N_8O_3Br_2$ | 74 (5 mMole) 2N HBr/AcOH | Example 1d 75.3 | C H N Br | 43.68 5.61 17.95 25.08 | 43.75 5.59 17.75 25.31 |
| 76f | 2HBr.H—D-Leu—Gly—Arg—8-NO$_2$—5-ChA $C_{23}H_{34}N_9O_5Br_2$ | 76 (5 mMole) 2N HBr/AcOH | Example 1d 72.7 | C H N Br | 40.75 5.10 18.95 23.30 | 40.84 5.07 18.64 23.63 |
| 85f | 2(CF$_3$COOH).H—Tyr—Gly—Arg—pNA $C_{27}H_{32}N_8O_{10}F_6$ | 85 (5 mMole) H$_2$F$_2$ (10 ml) | Examples 1d & 6 63.8 | C H N F | 43.37 4.35 15.24 14.88 | 43.67 4.34 15.09 15.35 |

The susceptibility of the tripeptide derivatives of the invention to factor Xa is illustrated numerically in the following Table 4 and compared with the that of the known prior art substrate Bz-Ile-Glu(Y-OH)-Gly-Arg-pNA.HCl.

TABLE 4

Activity of 1 ml of aqueous solution of bovine factor Xa and of factor Xa as obtained by activation of factor X in 1 ml of normal human blood plasma by means of RVV, expressed in nanomoles of split product H—$R^5$ released per minute

| substrate concentration $2 \times 10^{-4}$ | bovine factor Xa | human factor Xa |
|---|---|---|
| substrates according to examples | | |
| 1 | 2560 | 1520 |
| 2 | 1180 | 760 |
| 3 | 1405 | 985 |
| 4 | 1290 | 895 |
| 5 | 1140 | 815 |
| 6 | 2550 | 1520 |
| 7 | 950 | 705 |
| 8 | 2780 | 1568 |
| 9 | 2010 | 1105 |
| 10 | 1332 | 825 |
| 11 | 246 | 100 |
| 12 | 1960 | 1528 |
| 13 | 1526 | 1800 |
| 14 | 1936 | 1548 |
| 15 | 1436 | 1468 |
| 16 | 1630 | 1320 |
| 17 | 1320 | 1285 |
| 18 | 1385 | 1235 |
| 19 | 1290 | 660 |
| 20 | 1045 | 595 |
| 21 | 1675 | 795 |
| 22 | 1555 | 1432 |
| 23 | 985 | 580 |
| 24 | 2214 | 1000 |
| 25 | 2280 | 820 |
| 26 | 1205 | 495 |
| 27 | 1025 | 435 |
| 28 | 2028 | 1656 |
| 29 | 1940 | 1840 |
| 30 | 1986 | 1609 |
| 31 | 1160 | 1016 |
| 32 | 1070 | 695 |
| 33 | 1560 | 987 |
| 34 | 1040 | 560 |
| 35 | 1380 | 890 |
| 36 | 210 | 105 |
| 37 | 280 | 115 |
| 38 | 295 | 135 |
| 39 | 980 | 620 |
| 40 | 825 | 570 |
| 41 | 600 | 420 |
| 42 | 30 | 20 |
| 43 | 60 | 30 |
| 44 | 105 | 75 |
| 45 | 250 | 112 |
| 46 | 205 | 108 |
| 47 | 380 | 206 |
| 48 | 180 | 130 |
| 49 | 410 | 218 |
| 50 | 550 | 420 |
| 51 | 560 | 425 |
| 52 | 555 | 415 |
| 53 | 680 | 510 |
| 54 | 740 | 505 |
| 55 | 980 | 1200 |
| 56 | 850 | 1060 |
| 57 | 2440 | 1360 |
| 58 | 2540 | 1430 |
| 59 | 2260 | 1260 |
| 60 | 3230 | 1420 |
| 61 | 2660 | 1770 |
| 62 | 1420 | 995 |
| 63 | 1540 | 1065 |
| 64 | 1520 | 985 |
| 65 | 1280 | 1025 |
| 66 | 1370 | 965 |
| 67 | 1410 | 1005 |
| 68 | 1490 | 1010 |
| 69 | 1515 | 1030 |
| 70 | 1235 | 795 |
| 71 | 1280 | 810 |
| 72 | 1180 | 830 |
| 73 | 1265 | 875 |
| 74 | 1005 | 660 |
| 75 | 1145 | 745 |
| 76 | 965 | 715 |
| 77 | 1080 | 735 |
| 78 | 795 | 440 |
| 79 | 850 | 360 |
| 80 | 940 | 635 |
| 81 | 495 | 385 |
| 82 | 2530 | 1380 |
| 83 | 2480 | 1365 |
| 84 | 2210 | 1690 |
| 85 | 690 | 580 |
| 86 | 890 | 610 |
| 87 | 330 | 146 |
| 88 | 360 | 165 |
| 89 | 420 | 170 |
| 90 | 510 | 225 |
| 91 | 915 | 830 |
| 92 | 610 | 415 |
| 93 | 780 | 630 |
| 94 | 1020 | 845 |
| 95 | 750 | 465 |
| 96 | 830 | 505 |
| 97 | 1880 | 1420 |
| 98 | 1230 | 1080 |
| 99 | 1990 | 1515 |
| 100 | 1280 | 1055 |
| 101 | 2080 | 1290 |
| 102 | 1030 | 905 |
| 103 | 2260 | 1460 |
| Comparison substrate* | 490 | 820 |

*Bz—Ile—Glu(γ-OH)—Gly—Arg—pNA.HCl (disclosed in German patent application No. DE-OS 25 52 570)

The values of the factor Xa activity given in Table 4 were determined experimentally in the manner described hereinafter:

For determining the activity of bovine factor Xa 1.8 ml of TRIS-imidazole buffer having a pH of 8.4 and an ionic strength of 0.3 was well mixed at 37° C. with 0.025 ml of an aqueous solution of factor Xa preparation "Diagen" (furnisher: Diagnostic Reagents Ltd., Thame, Great Britain) obtained by dissolving the contents of one vial in 0.5 ml of water. To the mixture there was added 0.2 ml of a $2 \times 10^{-3}$ M aqueous solution of a substrate of the invention. Thereafter, the quantity of split product H—$R^5$ in nanomoles released per minute was determined, and the corresponding value of 1 ml of factor Xa solution was calculated.

For determining the activity of human factor Xa 0.01 ml of normal citrated plasma was mixed with 0.20 ml of a solution of Russel viper venom in TRIS-imidazole buffer having a pH of 8.4 and an ionic strength of 0.3 and containing 15 mmoles of $CaCl_2$ per ml. The mixture was incubated for 75 seconds at 37° C. in order to activate factor X present in the plasma and convert it completely into factor Xa. To the incubate there was added first 1.40 ml of TRIS-imidazole buffer (pH 8.4, ionic strength 0.3) heated to 37° C. and then 0.40 ml of a $2 \times 10^{-3}$ M aqueous solution of a substrate of the invention. Thereafter, the quantity of split produce H—$R^5$ in nanomoles released per minute was determined, and the corresponding value for 1 ml of citrated plasma was calculated.

I claim:

1. A process for quantitatively assaying factor Xa in a medium which contains factor Xa or in which factor Xa is formed or consumed, comprising reacting said medium with a tripeptide derivative having the formula

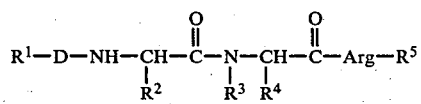

wherein $R^1$ represents an alkanoyl group which has 2 to 8 carbon atoms and which may carry an amino group in the ω-position, a phenylalkanoyl group which has 2 to 4 carbon atoms in the alkanoyl and the phenyl radical of which may be substituted with an amino group in the p-position, a cyclohexylcarbonyl group which may be substituted with an aminomethyl radical in the 4-position, a benzoyl group which may be substituted with methyl, amino or halogen in the o- or p-position, an alkoxycarbonyl group having 1 to 8 carbon atoms in the alkoxy group, a benzyloxycarbonyl group which may be substituted with methoxy, methyl or chlorine in the p-position, an alkanesulfonyl group having 1 to 4 carbon atoms, a phenylsulfonyl group which may be methylated in the p-position or an α- or β-naphthylsulfonyl group, $R^2$ represents a straight-chained or branched alkyl radical having 1 to 6 carbon atoms, a hydroxyalkyl radical having 1 to 2 carbon atoms, an alkoxyalkyl radical having 1 to 2 carbon atoms in the alkyl and 1 to 4 carbon atoms in the alkoxy, a benzyloxyalkyl radical having 1 to 2 carbon atoms in the alkyl, an ω-carboxyalkyl or ω-alkoxycarbonylalkyl radical which has 1 to 3 carbon atoms in the alkyl and the alkoxy group of which is straight-chained or branched and has 1 to 4 carbon atoms, or an ω-benzyloxycarbonylalkyl radical having 1 to 3 carbon atoms in the alkyl, or a cyclohexyl-, cyclohexylmethyl-, 4-hydroxycyclohexylmethyl-, phenyl-, benzyl-, 4-hydroxybenzyl- or imidazol-4-yl-methyl radical, $R^3$ represents a straight-chained or branched alkyl radical having 1 to 4 carbon atoms, $R^4$ represents hydrogen or a methyl or ethyl radical, and $R^5$ represents an amino group which is substituted with aromatic or heterocyclic radicals and which is capable of being split off hydrolytically with formation of a colored or fluorescent compound H—$R^5$, and salts thereof with acids and measuring, by photometric, spectrophotometric, fluorescence-spectrophotometric or electrochemical methods, the quantity of the colored or fluorescent split product H—$R^5$ released per time unit by the catalytic hydrolytic acid of factor Xa on the tripeptide derivative.

2. The process according to claim 1, wherein blood plasma of human beings or warm-blooded animals is treated with an activator in order to convert quantitatively the inactive factor X present in the plasma into the active factor Xa, said plasma containing active factor Xa is reacted with the said tripeptide derivative in a buffer system, and the quantity of split product H—$R^5$ released by the action of factor Xa from the tripeptide derivative per time unit is determined.

3. The process according to one of claims 1 or 2, wherein Russel viper venom (RVV) of a thromboplastin reagent is used as the activator.

4. A process for the quantitative assay of heparin in heparinized blood plasma via factor Xa, comprising: incubating a predetermined quantity of factor Xa with blood plasma in a buffer system, measuring the quantity of non-neutralized factor Xa by reacting the latter with a tripeptide derivative having the formula:

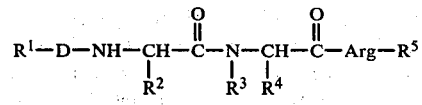

wherein $R^1$ represents an alkanoyl group which has 2 to 8 carbon atoms and which may carry an amino group in the ω-position, a phenylalkanoyl group which has 2 to 4 carbon atoms in the alkanoyl and the phenyl radical of which may be substituted with an amino group in the p-position, a cyclohexylcarbonyl group which may be substituted with an aminomethyl radical in the 4-position, a benzoyl group which may be substituted with methyl, amino or halogen in the o- or p-position, an alkoxycarbonyl group having 1 to 8 carbon atoms in the alkoxy group, a benzyloxycarbonyl group which may be substituted with methoxy, methyl or chlorine in the p-position, an alkanesulfonyl group having 1 to 4 carbon atoms, a phenylsulfonyl group, which may be methylated in the p-position or an α- or β-naphthylsulfonyl group, $R^2$ represents a straight-chained or branched alkyl radical having 1 to 6 carbon atoms, a hydroxyalkyl radical having 1 to 2 carbon atoms, an alkoxyalkyl radical having 1 to 2 carbon atoms in the alkyl and 1 to 4 carbon atoms in the alkoxy, a benzyloxyalkyl radical having 1 to 2 carbon atoms in the alkyl, an ω-carboxyalkyl or ω-alkoxycarbonylalkyl radical which has 1 to 3 carbon atoms in the alkyl and the alkoxy group of which is straight-chained or branched and has 1 to 4 carbon atoms, or an ω-benzyloxycarbonylalkyl radical having 1 to 3 carbon atoms in the alkyl, or a cyclohexyl-, cyclohexylmethyl-, 4-hydroxycyclohexylmethyl-, phenyl-, benzyl-, 4-hydroxybenzyl- or imidazol-4-yl-methyl radical, $R^3$ represents a straight-chained or branched alkyl radical having 1 to 4 carbon atoms, $R^4$ represents hydrogen or a methyl or ethyl radical, and $R^5$ represents an amino group which is substituted with aromatic or heterocyclic radicals and which is capable of being split off hydrolytically with formation of a colored or fluorescent compound H—$R^5$, and salts thereof with acids, determining the quantity of split product H—$R^5$ released per time unit and determining the heparin level from the difference between the quantity of factor Xa initially used and the residual quantity of factor Xa.

5. A process for the quantitative assay of antifactor Xa in human blood plasma via factor Xa, comprising: preparing a test sample by diluting citrated human plasma with a buffer solution, adding heparin and then factor Xa to the dilute solution and adding to the mixture a tripeptide derivative, having the formula:

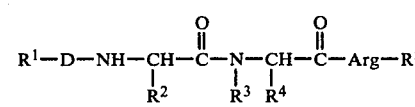

wherein $R^1$ represents an alkanoyl group which has 2 to 8 carbon atoms and which may carry an amino group in the α-position, a phenylalkanoyl group which has 2 to 4 carbon atoms in the alkanoyl and the phenyl radical of which may be substituted with an amino group in the p-position, a cyclohexylcarbonyl group which may be substituted with an aminomethyl radical in the 4-position, a benzoyl group which may be substituted with methyl, amino or halogen in the o- or p-position, an alkoxycarbonyl group having 1 to 8 carbon atoms in the alkoxy group, a benzyloxycarbonyl group which may be substituted with methoxy, methyl or chlorine in the p-position, an alkanesulfonyl group having 1 to 4 carbon atoms, a phenylsulfonyl group which may be methylated in the p-position or an α- or β-naphthylsulfonyl group, $R^2$ represents a straight-chained or branched alkyl radical having 1 to 6 carbon atoms, a hydroxyalkyl radical having 1 to 2 carbon atoms, an alkoxyalkyl radical having 1 to 2 carbon atoms in the alkyl and 1 to 4 carbon atoms in the alkoxy, a benzyloxyalkyl radical having 1 to 2 carbon atoms in the alkyl, an α-carboxyalkyl or α-alkoxycarbonylalkyl radical which has 1 to 3 carbon atoms in the alkyl and the alkoxy group of which is straight-chained or branched and has 1 to 4 carbon atoms, or an ω-benzyloxycarbonylalkyl radical having 1 to 3 carbon atoms in the alkyl, or a cyclohexyl-cyclohexylmethyl-, 4-hydroxycyclohexylmethyl-, phenyl-, benzyl-, 4-hydroxybenzyl- or imidazol-4-yl-methyl radical, $R^3$ represents a straight-chained or branched alkyl radical having 1 to 4 carbon atoms, $R^4$ represents hydrogen or a methyl or ethyl radical, and $R^5$ represents an amino group which is substituted with aromatic or heterocyclic radicals and which is capable of being split off hydrolytically with formation of a colored or fluorescent compounds $H—R^5$, and salts thereof with acids, preparing a blank test sample in the same manner, but using the same volumetric amount of buffer instead of dilute citrated human plasma, determining for both samples the increase in the optical density per minute caused by the formation of split product $H—R^5$, and determining the quantity of factor Xa inhibited by the antifactor Xa-heparin complex and therefrom the quantity of antifactor Xa present in the dilute citrated human plasma from the difference of the increase in the optical density of the blank test sample per minute and the increase in the optical density of the test sample per minute.

6. The process according to one of claims 1, 2, 4 or 5, wherein if $R^5$ is a p-nitrophenylamino, 1-carboxy-2-nitrophen-5-yl-amino, 1-sulfo-2-nitro-phen-5-yl-amino, 5-nitro-α-naphthyl-amino or 8-nitro-quinon-5-yl-amino group, the split product $H—R^5$, before the measurement, is converted into a more intensely colored compound by coupling with a diazo compound.

7. The process according to one of claims 1, 4 or 5, wherein the $R^5$ group of the tripeptide derivative is a p-nitrophenylamino, 1-carboxy-2-nitrogen-5-yl-amino, 1-sulfo-2-nitrophen-5-yl-amino, β-naphthylamino, 4-methoxy-β-naphthylamino, 5-nitro-α-naphthylamino, quinon-5-yl-amino, 8-nitro-quinon-5-yl-amino, 4-methyl-coumar-7-yl-amino, or 1,3-di(methoxycarbonyl)-phen-5-yl-amino group derived from 5-amino-isophthalic acid dimethyl ester.

8. The process according to one of claims 1, 4 or 5 wherein the guanidino group of arginine is stabilized by protonation with acetic acid.

9. The process according to one of claims 1, 4 or 5 wherein the tripeptide derivative is Cbo-D-Leu-Gly-Arg-pNA.AcOH, Cbo-D-Leu-Sar-Arg-pNA.AcOH, Cbo-D-Ph'Gly-Gly-Arg-pNA.AcOH, Cbo-D-Nleu-Gly-Arg-pNA.AcOH, Cbo-D-Nleu-Sar-Arg-pNA.AcOH, Cbo-D-Nval-Gly-Arg-pNA.AcOH, Cbo-D-CHA-Gly-Arg-pNA.AcOH, Cbo-D-CHA-Sar-Arg-pNA.AcOH, Cbo-D-CHT-Gly-Arg-pNA.AcOH, Cbo-D-CHT-Sar-Arg-pNA.AcOH, Cbo-D-CHG-Gly-Arg-pNA.AcoH, $CH_3SO_2$-D-Nleu-Gly-Arg-pNA.AcOH, isobutoxy-CO-D-Nleu-Gly-Arg-pNA.AcOH, BOC-D-Leu-Gly-Arg-pNA.HBr, 4-MeO-Cbo-D-Leu-Gly-Arg-pNA.HBr, $CH_3O$-CO-D-CHA-Gly-Arg-pNA.AcOH, $C_2H_5O$-CO-D-CHA-Gly-Arg-pNA.AcOH, $CH_3SO_2$-D-CHA-Gly-Arg-pNA.AcOH, 4-Me-Cbo-D-Leu-Gly-Arg-pNA.AcOH, 4-Cl-Cbo-D-Leu-Gly-Arg-pNA.AcOH or BOC-D-(α)-AOA-Gly-Arg-pNA.AcOH.

* * * * *

UNITED STATES PATENT AND TRADEMARK OFFICE
CERTIFICATE OF CORRECTION

PATENT NO. : 4,480,030
DATED : October 30, 1984
INVENTOR(S) : Lars G. Svendsen

It is certified that error appears in the above-identified patent and that said Letters Patent is hereby corrected as shown below:

Column 33, line 51, "hydrolytic acid" should be -- hydrolytic action--.

Column 35, line 15, "$\alpha$-carboxyal"- should be -- $\omega$-carboxyal- --.

Column 35, line 16, "$\alpha$-alkoxycarbonylalkyl" should be --$\omega$-alkoxycarbonylalkyl--.

Signed and Sealed this

Seventh Day of January 1986

[SEAL]

Attest:

DONALD J. QUIGG

Attesting Officer    Commissioner of Patents and Trademarks